United States Patent
Chu et al.

(10) Patent No.: US 10,194,927 B2
(45) Date of Patent: Feb. 5, 2019

(54) RETRIEVAL DEVICES AND RELATED METHODS OF USE

(71) Applicant: Boston Scientific Scimed, Inc., Maple Grove, MN (US)

(72) Inventors: Michael S. H. Chu, Brookline, MA (US); Ken Flynn, Woburn, MA (US); Mark Andrew Hera, Holden, MA (US); Jerry Timothy Long, Jr., Jamaica Plain, MA (US); Lauren Mary Moscato, Boston, MA (US); Peter J. Pereira, Mendon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 363 days.

(21) Appl. No.: 14/989,421

(22) Filed: Jan. 6, 2016

(65) Prior Publication Data

US 2016/0199079 A1    Jul. 14, 2016

Related U.S. Application Data

(60) Provisional application No. 62/101,759, filed on Jan. 9, 2015.

(51) Int. Cl.
*A61B 17/221* (2006.01)

(52) U.S. Cl.
CPC .... *A61B 17/221* (2013.01); *A61B 2017/2215* (2013.01)

(58) Field of Classification Search
CPC .................. A61B 17/221; A61B 2017/2215
USPC ................................ 606/113, 114, 127, 128
See application file for complete search history.

(56) References Cited

U.S. PATENT DOCUMENTS

| 5,201,741 | A | * | 4/1993 | Dulebohn ........ A61B 17/32056 |
| | | | | 606/110 |
| 5,906,622 | A | | 5/1999 | Lippitt et al. |
| 5,924,175 | A | | 7/1999 | Lippitt et al. |
| 7,041,108 | B2 | * | 5/2006 | Lippitt ................. A61B 17/221 |
| | | | | 604/264 |
| 7,210,210 | B2 | | 5/2007 | Lippitt et al. |
| 2002/0133170 | A1 | | 9/2002 | Tsuruta |
| 2003/0225419 | A1 | | 12/2003 | Lippitt et al. |
| 2009/0082780 | A1 | * | 3/2009 | Lu ........................ A61B 17/221 |
| | | | | 606/127 |
| 2015/0066047 | A1 | | 3/2015 | Chu et al. |
| 2015/0066049 | A1 | | 3/2015 | Chu |
| 2015/0148814 | A1 | | 5/2015 | Chu |

(Continued)

FOREIGN PATENT DOCUMENTS

| EP | 2 949 277 A1 | 12/2015 |
| WO | WO 98/48710 A1 | 11/1998 |
| WO | WO 2015/106131 | 7/2015 |

*Primary Examiner* — Kathleen Holwerda
(74) *Attorney, Agent, or Firm* — Bookoff McAndrews, PLLC

(57) ABSTRACT

A retrieval device having a contracted state and an expanded state may include a sheath, and at least three support members each having at least two lumens, a proximal end fixed to the sheath, and a distal end movable relative to the sheath. The retrieval device may also include at least three movable members movable relative to the support members. Each movable member may extend through a lumen of one support member of the at least three support members and through a lumen of a different support member of the at least three support members.

16 Claims, 11 Drawing Sheets

(56) References Cited

U.S. PATENT DOCUMENTS

| | | |
|---|---|---|
| 2015/0164522 A1 | 6/2015 | Budiman et al. |
| 2015/0190157 A1 | 7/2015 | Chu |
| 2015/0190190 A1 | 7/2015 | Chu |
| 2015/0196311 A1 | 7/2015 | Chu |
| 2015/0327878 A1 | 11/2015 | Chu et al. |

* cited by examiner

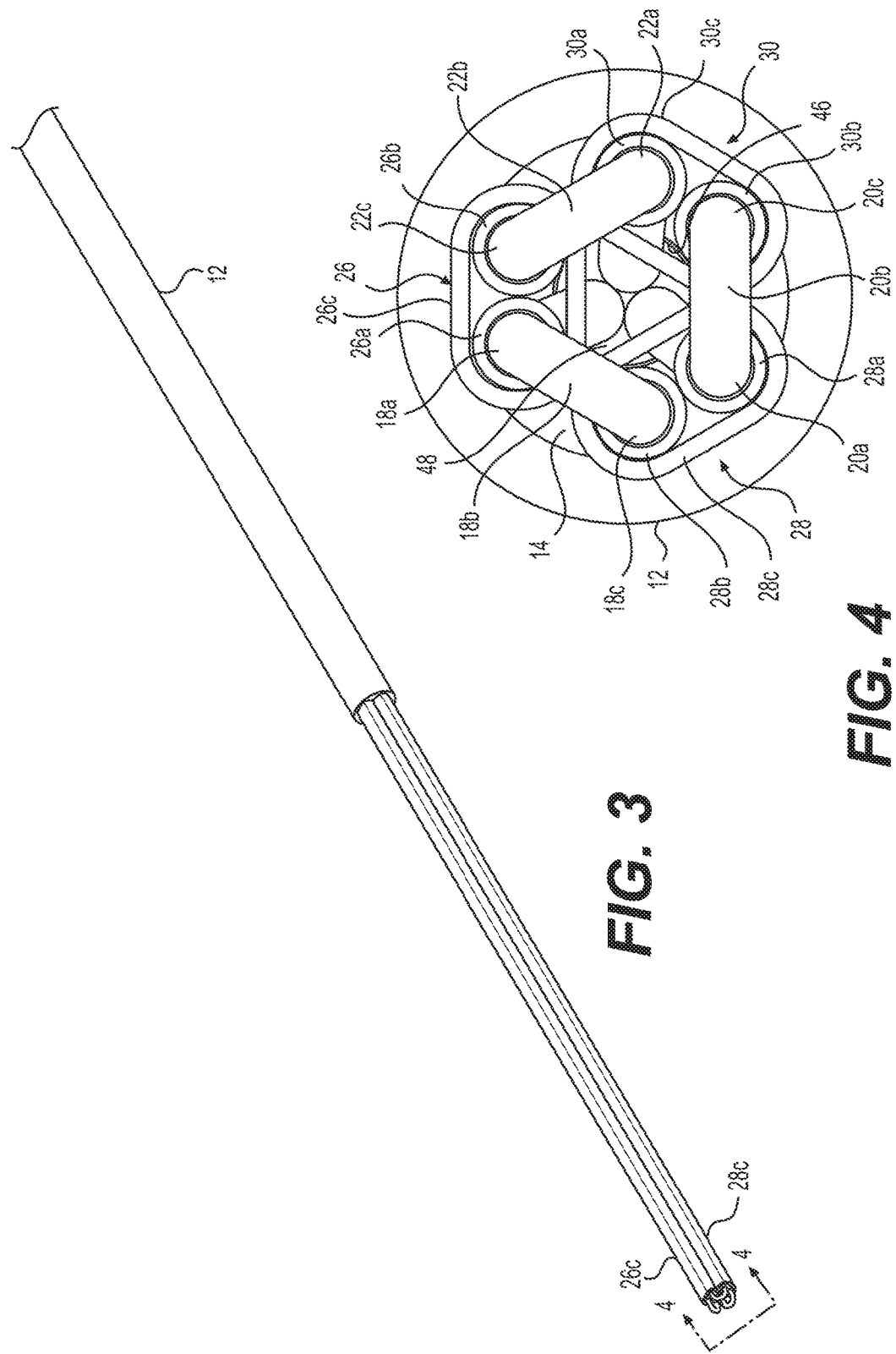

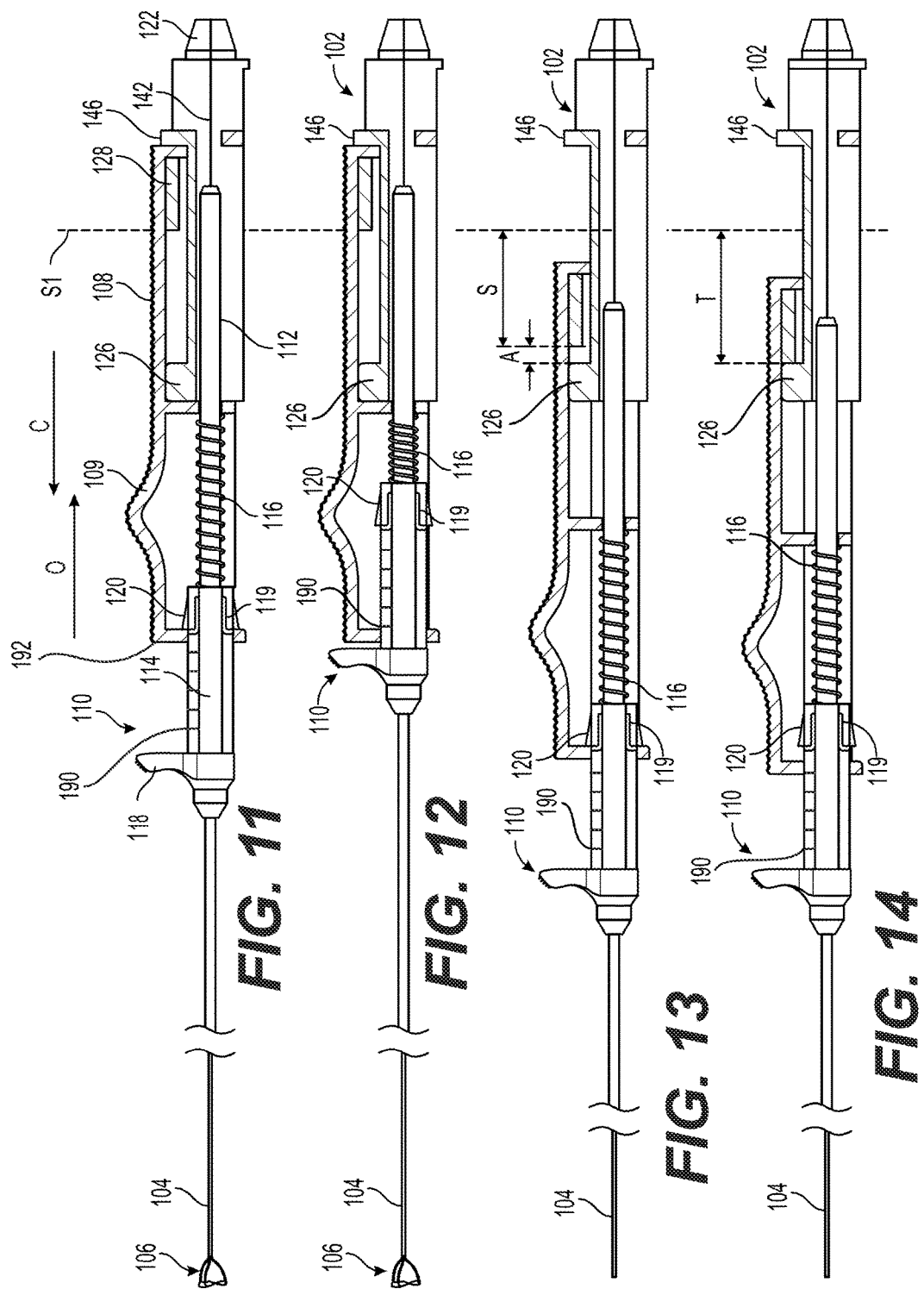

RETRIEVAL DEVICES AND RELATED METHODS OF USE

CROSS-REFERENCE TO RELATED APPLICATION(S)

This patent application claims the benefit of priority under 35 U.S.C § 119 to U.S. Provisional Patent Application No. 62/101,759, filed on Jan. 9, 2015, the entirety of which is incorporated herein by reference.

TECHNICAL FIELD

Various examples of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PCNL") procedure. Further, lithotripsy and ureteroscopy, for example, are used to treat urinary calculi (e.g., kidney stones) in the ureter of a patient.

Retrieval devices may include end effectors for manipulating objects. An exemplary end effector may have a plurality of arms that support a front loop that forms when the end effector is opened. The size of the front loop may limit the size of an object that can be captured, repositioned, and/or released from the end effector. For some procedures, there may be a need to increase the size of a front loop of an end effector to facilitate the capturing, repositioning, and/or releasing of larger objects. It may also be desirable to have an end effector close back down to a low-profile state to facilitate insertion and withdrawal of the end effector into and from a target area, and/or to capture, reposition, and/or release smaller objects. Thus, there remains a need for retrieval devices with improved capabilities.

Further, known medical retrieval devices are complex, requiring many components and labor-intensive manufacturing processes. The assembly of small parts often requires visual magnification and specialized training. The available joining mechanisms often increase the profile of the medical retrieval devices beyond optimal design parameters, and are often the weakest structural points. These drawbacks result in medical retrieval devices that are bulky, expensive, and prone to failure.

Further, it is often desirable to measure the diameter of kidney stones or stone fragments before, during, or after removal from the patient. This measurement helps the urologist determine how to treat the stone and how to counsel the patient after completion of the procedure. Currently, urologists roughly estimate the diameter of a stone or fragment by visually comparing a reference object of known size (e.g., a retrieval device or guidewire diameter) to the stone under direct endoscopic visualization. This technique results in widely varying and often inaccurate estimates of stone size.

Thus, there remains a need for improved medical retrieval devices having reduced profiles and fewer components, and for improved mechanisms for determining the size of a stone in vivo.

SUMMARY

A retrieval device having a contracted state and an expanded state may include a sheath, and at least three support members each having at least two lumens, a proximal end fixed to the sheath, and a distal end movable relative to the sheath. The retrieval device may also include at least three movable members movable relative to the support members. Each movable member may extend through a lumen of one support member of the at least three support members and through a lumen of a different support member of the at least three support members.

Each support member may include a first tube defining one lumen of the at least two lumens, and a second tube defining another lumen of the at least two lumens. The first and second tubes of a given support member may be fixed relative to one another. The first and second tubes of a given support member may be substantially parallel to one another. Each support member may further include a reinforcing member disposed around the first and second tubes. The reinforcing member may be disposed at a distal end of the first and second tubes. Each support member may include a portion extending distally from the sheath that remains uncovered by the reinforcing member. Each of the at least three movable members may be configured to slide distally within one or more of the at least three support members during transition of the retrieval device from the contracted state to the expanded state. Each support member may be parallel to a longitudinal axis of the sheath while the retrieval device is in the contracted state. Each support member may be configured to bow radially outward from a longitudinal axis of the sheath in the expanded state. The sheath may encompass at least a portion of the movable members and at least a portion of the support members. The retrieval device may further include a stop located at an end of at least one movable member to restrict movement of the end after moving a distance distally. The stop may include a coupling securing ends of the at least three movable members together. Each of the at least three movable members may include a U-shaped bend located distally of the distal ends of the at least three support members. The U-shaped bend may be preformed and urge the support members toward the contracted state.

A retrieval device may include a sheath, and at least three pairs of tubes disposed at a distal end of the sheath. Each of the pairs of tubes may be movable between a contracted configuration and an expanded configuration. Each of the pairs of tubes may be parallel to a longitudinal axis of the sheath in the contracted configuration, and may be configured to bow radially outward from the longitudinal axis of the sheath in the expanded configuration. The retrieval device may include at least three movable members. Each movable member may form a bridge between two different pairs of tubes of the at least three pairs of tubes.

The tubes of a given pair of tubes of the at least three pairs of tubes may be fixed relative to one another. The retrieval device may include three bridges formed by the at least three movable members. The three bridges may form a distally-facing loop when the pairs of tubes are in the expanded configuration. Each bridge may form a side loop with the two different pairs of tubes that the bridge is between.

A method for retrieving an object using a retrieval device including a sheath, at least three support members each having at least two lumens, a proximal end fixed to the sheath, and a distal end movable relative to the sheath, and at least three movable members movable relative to the support members, each movable member extending through a lumen of one support member of the at least three support members and through a lumen of a different support member of the at least three support members, may include moving the movable members distally to transition the retrieval device from a contracted state to an expanded state.

It is understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIG. 3 is a perspective view of the distal end of the retrieval device of FIG. 1 in a retracted state, in accordance with examples of the present disclosure.

FIG. 4 is a distal end view of the retrieval device of FIG. 1, in accordance with examples of the present disclosure.

FIG. 11 is a partial cross-sectional side view of portions of the retrieval device of FIG. 7 in an extended state.

FIG. 12 is a partial cross-sectional side view of portions of the retrieval device of FIG. 7 in a further extended state.

FIG. 13 is a partial cross-sectional side view of portions of the retrieval device of FIG. 7, in a retracted state.

FIG. 14 is a partial cross-sectional side view of a portion of a retrieval device of FIG. 7 in a further retracted state.

DETAILED DESCRIPTION

Overview

The present disclosure is drawn to retrieval devices and related systems and methods. Reference will now be made in detail to examples of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

Examples

Figure 1:
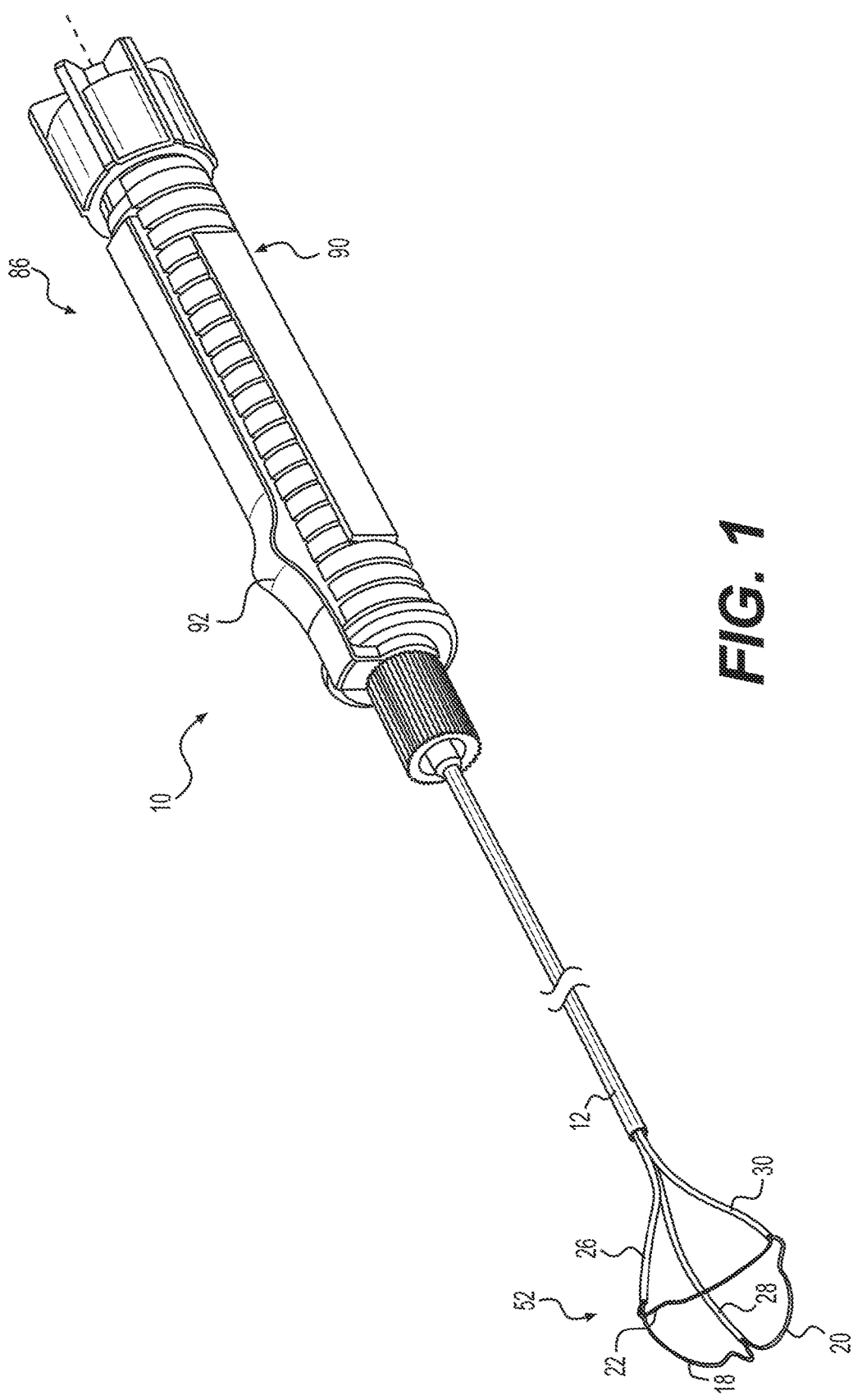
FIG. 1 is a full view of a retrieval device in an extended and expanded state.
Figure 5:
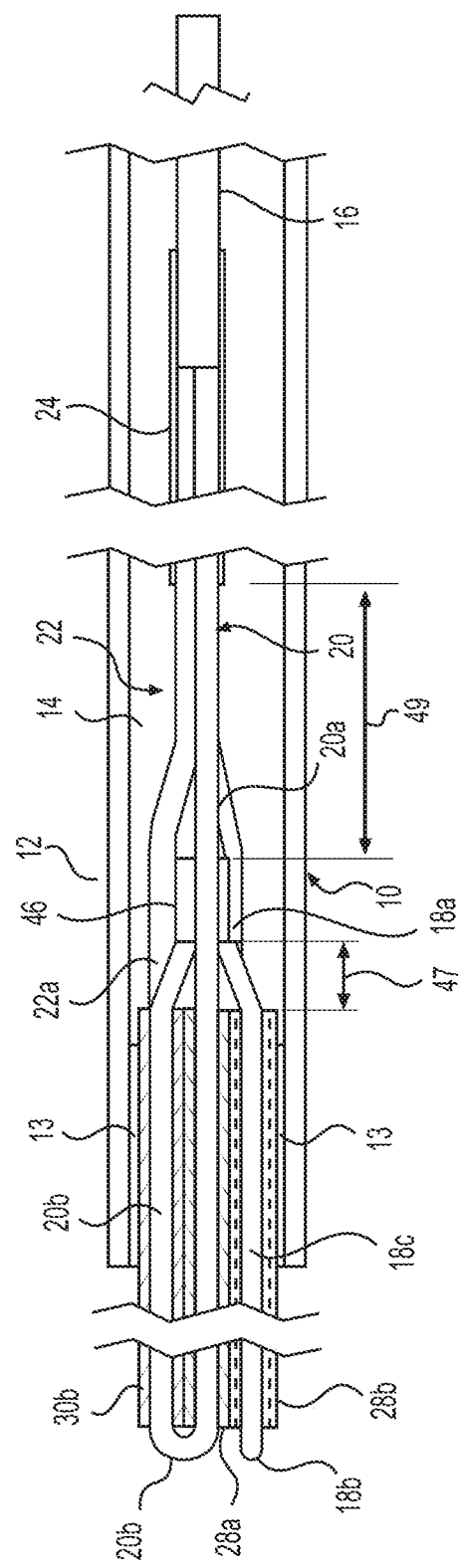
FIG. 5 is a side and partial view of a retrieval device including an end effector in a retracted and contracted state, in accordance with examples of the present disclosure.

FIG. 1 shows a full retrieval device 10, and FIGS. 2-5 show portions of the retrieval device 10. Referring to FIG. 1, the device 10 may include a basket portion or grasper portion 52 including a plurality of movable members 18, 20, and 22, and a plurality of support members 26, 28, and 30. The support members 26, 28, and 30 may be coupled to an outer sheath 12 and back to a handle assembly 90. The movable members 18, 20, and 22 may be coupled back to the handle assembly 90 through the support members 26, 28, and 30 and the outer sheath 12. As explained in more detail below, movement of an actuator 92 of the handle assembly 90 may provide relative movement between the movable members 18, 20, and 22, and support members 26, 28, and 30 to transition the grasper portion 52 between an expanded state (FIGS. 1 and 2) and a contracted state (FIGS. 3-5).

Referring to FIGS. 3-5, the outer sheath 12 of retrieval device 10 may include a lumen 14 extending longitudinally therethrough. The outer sheath 12 may be, for example, a hollow tube of about 1.7 French, although the dimensions may differ based on the type of procedure being performed with the retrieval device 10. In another example, the outer sheath 12 may be a hollow tube of about 1.9 French. The outer sheath 12 may be made of a polymer material or combination of materials. A proximal portion of the outer sheath 12 may be made of a different material than a distal portion of the outer sheath 12. For example, the distal portion of the outer sheath 12 may be made of a material that is more flexible than the material of the proximal portion of the outer sheath 12.

The retrieval device 10 may also include a drive member or shaft 16. The drive member 16 may extend through the lumen 14 of the outer sheath 12. The drive member 16 may be elongated, and may include, for example, a wire, braid, cable, shaft, and/or any other suitable drive member configured to receive or transfer compression, tension, and/or torsional forces. The drive member 16 may have any suitable cross-sectional shape, including cylindrical, elliptical, polygonal, and/or irregular. The drive member 16 may be made of metals, polymers, or a combination of materials. It is also contemplated that the drive member 16 may have a diameter of approximately 0.0125 inches (0.03175 centimeters). The drive member 16 may have other diameters, however, depending on the type of procedure being performed with the retrieval device 10.

The movable members of retrieval device 10 may include a first movable member 18, a second movable member 20, and a third movable member 22. The first movable member 18 may include a first leg 18a, a reverse or U-shaped bend 18b, and a second leg 18c. Similarly, the second movable member 20 may include a first leg 20a, a reverse or U-shaped bend 20b, and a second leg 20c. The third movable member 22 may also include a first leg 22a, a reverse or U-shaped bend 22b, and a second leg 22c. While three movable members 18, 20, and 22 are shown, one or more additional movable members may also be included. The bends 18b, 20b, and 22b may be disposed between respective first and second legs 18a and 18c, 20a and 20c, and 22a and 22c, respectively.

Each of the movable members 18, 20, and 22 may be formed of any suitable material including, but not limited to, metals, polymers, or a combination of materials. For example, one or more of the movable members 18, 20, and 22 may be formed with a shape memory material, such as Nitinol, and may be treated to possess an internal bias causing one or more of the movable members 18, 20, and 22 to move to a preselected position in the absence of an urging force. For example, the U-shaped bends 18b, 20b, 22b of the movable members 18, 20, and 22 may be preformed such as by heat setting into the U-shaped bend shape. This preformed U-shaped bend 18b, 20b, 22b may facilitate a clamping of the distal ends of the support members together in the contracted state (FIGS. 3-5). One or more of the movable members 18, 20, and 22 may be a wire, braid, cable, or shaft having any suitable diameter, such as a diameter of about 0.003 inches (0.00762 centimeters), although other suitable diameters may alternatively be utilized.

Each of the movable members 18, 20, and 22 may have any suitable cross-sectional shape, including cylindrical, elliptical, polygonal, and/or irregular. One or more of the movable members 18, 20, and 22 may include a portion flattened, machined, extruded, drawn, and/or etched into a different profile than a remaining portion. One or more of the movable members 18, 20, and 22 may be slotted to allow deflection or directional bending. The exterior surfaces of one or more of the movable members 18, 20, and 22 may be roughened, notched, slotted, etched, sand-blasted, or otherwise modified to provide a better gripping surface.

The movable members 18, 20, and 22 may be attached to the drive member 16 at a first end. For example, proximal ends of the first legs 18a, 20a, and 22a may be attached to the distal end of the drive member 16. The attachment may be provided by one or more of a splice joint, adhesives, melting, welding, crimping, and/or any other suitable attachment mechanism. It is also contemplated that a sleeve 24 may be placed over the proximal portions of the first legs 18a, 20a, and 22a, and the distal portion of the drive member 16 to secure the elements together. The sleeve 24 may be made of a polytetrafluoroethylene like TEFLON. The sleeve 24 may be heat shrinkable onto the first legs 18a, 20a, and 22a, and the drive member 16. The sleeve 24 may have a length of about 11.5 centimeters, but it should be understood that the length and other sleeve dimensions may vary based on the type of procedure being performed with the retrieval device 10. The sleeve 24 may help gather the first legs 18a, 20a, and 22a, to avoid radially outward movement of the legs when pushed distally by the drive member 16, giving the gathered portions added strength. The proximal portions of each of the first legs 18a, 20a, and 22a may contact the proximal portions of the other first legs. Longitudinal axes of the proximal portions of the first legs 18a, 20a, and 22a may be substantially parallel.

The support members of the retrieval device 10 may include a first support member 26, a second support member 28, and a third support member 30. The support members 26, 28, and 30 each may include two tubes that are substantially parallel to one another. For example, support member 26 may include a first tube 26a and a second tube 26b. Each of the first and second tubes 26a, 26b may have any suitable cross-sectional shape, including circular, oval, elliptical, polygonal, and/or irregular. One or more of first and second tubes 26a, 26b may include a portion flattened, machined, extruded, drawn, and/or etched into a different profile than a remaining portion. One or more of first and second tubes 26a, 26b may be slotted to allow deflection or directional bending. One or more of first and second tubes 26a, 26b may have an inner diameter of about 0.0034 inches (0.008636 centimeters), an outer diameter of about 0.0046 inches (0.011684 centimeters), a wall thickness of about 0.0006 inches (0.001524 centimeters), and/or a length of about 19.5 millimeters, although other suitable dimensions may alternatively be utilized. The exterior surfaces of one or more of first and second tubes 26a, 26b may be roughened, notched, slotted, etched, sand-blasted, or otherwise modified to provide a better gripping surface. The first and second tubes 26a, 26b may be made of heat shrink tubes, and made of any suitable material or combination of materials, including a polymer such as polyimide, or polyethylene terephthalate. Second support member 28 may include a first tube 28a and a second tube 28b. Similarly, third support member 30 may include a first tube 30a and a second tube 30b. Tubes 28a, 28b, 30a, and 30b may be substantially similar to first and second tubes 26a and 26b described above.

The support members 26, 28, and 30 may be disposed circumferentially about the longitudinal axis of the outer sheath 12. The longitudinal axes of the support members may be disposed at equal intervals circumferentially about the longitudinal axis. It should, however, be noted that any other suitable number of support members and spacing configurations may alternatively be utilized. As shown in FIGS. 3-5, each of the movable members 18, 20, and 22 may extend distally from a first, proximal end thereof that is coupled to the drive member 16, extend distally through a first or second tube of a support member 26, 28, and 30 along the first leg 18a, 20a, and 22a, form the preformed U-shaped bend 18b, 20b, and 22b, and extend proximally through a first or second tube of a different support member 26, 28, and 30 along the second leg 18c, 20c, and 22c. In this configuration, the preformed U-shaped bend may confine or urge the support members 26, 28, and 30 toward a low profile in the contracted state.

The movable members 18, 20, and 22, and the support members 26, 28, and 30, may be heat treated simultaneously, and the material for the movable members 18, 20, and 22 and the support members 26, 28, and 30 may be selected such that the support members 26, 28, and 30 will not melt during heat treatment of the movable members 18, 20, and 22. While three support members 26, 28, and 30 are shown, one or more additional support members may be used.

Proximal portions of the support members 26, 28, and 30 (e.g., proximal portions of the respective first and second tubes 26a and 26b, 28a and 28b, and 30a and 30b) may extend through the lumen 14, and may be covered by the outer sheath 12. For example, a length of about 10 millimeters of one or more of the first and second tubes 26a and 26b, 28a and 28b, and 30a and 30b may be covered by the outer sheath 12, leaving a length of about 9.5 millimeters exposed distal to the outer sheath 12.

Distal portions of the first and second tubes 26a and 26b, 28a and 28b, and 30a and 30b may extend distally out of the lumen 14 and away from the distal end of the outer sheath 12. The distal portions may be configured to move towards and away from the longitudinal axis of the outer sheath 12. The number of support members 26, 28, and 30 may be equal to the number of movable members 18, 20, and 22. That is, the combined number of first and second tubes 26a, 26b, 28a, 28b, 30a, and 30b may be double the number of movable members 18, 20, and 22. Alternatively, the number of support members 26, 28, and 30 may be less than the movable members 18, 20, and 22. For example, a single movable member may form two of the movable members 18, 20, and 22, for use with three support members.

The distal portions of the support members 26, 28, and 30 may be at least partially covered by a reinforcing member. For example, a reinforcing member 26c may cover substantially all of the distal portions of first and second tubes 26a and 26b as shown in FIG. 3. That is, reinforcing member 26c may be disposed around the portions of first and second tubes 26a and 26b that extend from distally away from the distal end of outer sheath 12. First and second tubes 26a and 26b may be generally fixed relative to one another due to the presence of reinforcing member 26c. Reinforcing member 26c may be a heat shrink tube with a wall thickness of about 0.001 inches (0.00254 centimeters), although other suitable dimensions are also contemplated. Reinforcing member 26c may be formed of polyester and/or any other suitable material. Reinforcing member 26c may have a circular, ovular, or other suitable cross-sectional profile prior to heat shrinking. After heat is applied, reinforcing member 26c may maintain a generally ovular shape. Alternatively, reinforcing member 26c may have a generally ovular shape, and may be glued or otherwise secured to the outer surfaces of first and second tubes 26a and 26b. A reinforcing member 28c may cover substantially all of the distal portions of first and second tubes 28a and 28b, and a reinforcing member 30c may cover substantially all of the distal portions of first and second tubes 30a and 30b. Reinforcing members 28c and 30c may be substantially similar to reinforcing member 26c. The presence of reinforcing members 26c, 28c, and 30c may help prevent movable members 18, 20, and/or 22 from splitting the distal ends of support members 26, 28, and 30 during retraction and expansion of basket 52. It is further noted that reinforcing members 26c, 28c, and 30c have been omitted from FIG. 5 for clarity.

Each of the three support members 26, 28, and 30 may be coupled to the outer sheath 12 via their respective first and second tubes. For example, proximal ends of the first tubes 26a, 28a, and 30a, and the proximal ends of second tubes 26b, 28b, and 30b that are covered by the distal end of the outer sheath 12 may be fixedly coupled to the distal end of the outer sheath 12 by an adhesive 13, such as an ultraviolet light curable adhesive or cyanoacrylate. Additionally or alternatively, the distal end of the outer sheath 12 may be fixedly coupled to the proximal ends of the first and second tubes of support members 26, 28, and 30 by heat shrinking or by using a coupling tube glued at both ends. The coupling may keep the proximal ends of the first and second tubes of support members 26, 28, and 30 stationary relative to the distal end of outer sheath 12, while allowing the distal ends of the support members 26, 28, and 30 to move relative to the distal end of the outer sheath 12 and relative to one another.

The first leg 18a may extend distally from the drive member 16, and may enter a lumen at the proximal end of the first tube 26a of support member 26. The first leg 18a may extend distally through the first tube 26a, and may exit the distal end of the first tube 26a. There, the first leg 18a may transition into the bend 18b. The bend 18b may transition into the second leg 18c. The second leg 18c may enter a lumen at the distal end of second tube 28b of the second support member 28. The second leg 18c may extend proximally through the second tube 28b, and may exit the proximal end of the second tube 28b.

The first leg 20a may extend distally from the drive member 16, and may enter a lumen at the proximal end of the first tube 28a of the second support member 28. The first leg 20a may extend distally through the first tube 28a, and may exit the distal end of the first tube 28a. There, the first leg 20a may transition into the bend 20b. The bend 20b may transition into the second leg 20c. The second leg 20c may enter a lumen at the distal end of the second tube 30b of the third support member 30. The second leg 20c may extend proximally through the second tube 30b, and may exit the proximal end of the second tube 30b.

The first leg 22a may extend distally from the drive member 16, and may enter a lumen at the proximal end of the first tube 30a of the third support member 30. The first leg 22a may extend distally through the first tube 30a, and may exit the distal end of the first tube 30a. There, the first leg 22a may transition into the bend 22b. The bend 22b may transition into the second leg 22c. The second leg 22c may enter a lumen at the distal end of the second tube 26b of the first support member 26. The second leg 22c may extend proximally through the second tube 26b, and may exit the proximal end of the second tube 26b.

Alternatively, it is contemplated that the first leg 18a may extend distally through the second tube 28b, and the second leg 18c may extend proximally through the first tube 26a. The first leg 20a may extend distally through the second tube 30b, and the second leg 20c may extend proximally through the first tube 28a. The first leg 22a may extend distally through the second tube 26b, and the second leg 22c may extend proximally through the first tube 30a.

One or more of the proximal or second ends of the second legs 18c, 20c, and 22c may include a movable stop sized to abut or engage a proximal end of a support member 26, 28, and 30 after moving a distance 47 distally during movement of the retrieval device toward the expanded state. The movable stop may be formed in a number of different ways. An exemplary movable stop is shown in FIGS. 4 and 5, and includes a coupler 46 in the form of a tube including a lumen 48 configured to receive proximal ends of the second legs 18c, 20c, and 22c. The second legs 18c, 20c, and 22c may be attached to each other within the coupler 46 and attached to the coupler 46. For example, each of the second legs 18c, 20c, and 22c may be attached to each other and the coupler 46 by adhesive, melting, welding, crimping, friction fit, heat-shrinking the coupler 46, and/or any other suitable form of attachment. Portions of the first legs 18a, 20a, and 22a may extend along the side of the coupler 46, and may contact the exterior surface of the coupler 46. The coupler 46 may space portions of the first legs 18a, 20a, and 22a apart from the longitudinal axis of the outer sheath 12, to help guide the first legs 18a, 20a, and 22a into the support members 26, 28, and 30 (via first tubes 26a, 28a, and 30a, respectively).

Alternatively, the movable stop could be formed by replacing the two movable members 18 and 20 with a single moveable member having a U-shaped bend replacing the proximal ends of the second legs 18c and 20c. In this arrangement, the U-shaped bend could form the movable stop of the movable members against the proximal end of the support members 26, 28, and 30 during a first phase of the expansion of the retrieval device 10. Further, the second leg 22c could be coupled to the U-shaped bend to limit its travel. Alternatively, proximal U-shaped or L-shaped hooks, or any other type of obstruction (not shown) could be provided on one, two, or all of the second legs 18c, 20c, and 22c to form the movable stop for abutting or engaging the support members 26, 28, and 30 and limiting movement of the second legs 18c, 20c, and 22c to the distance 47 during the first phase of expansion of the retrieval device 10.

The movable members 18, 20, and 22, and the support members 26, 28, and 30, may form an end effector 50. The end effector 50 may together form the basket or grasper portion 52. In FIGS. 3-5, the grasper portion 52 is shown in the retracted and contracted state. The grasper portion 52 may be moved into its retracted and contracted state by moving the drive member 16 proximally relative to the outer sheath 12, or moving the sheath 12 distally relative to the drive member 16. Reference to "movable" members 26, 28, 30 refers to the relative movement of members 26, 28, 30 in relation to other elements of the device 10, and thus it is understood that the term "movable" in movable members 26, 28, and 30 includes the members being axially stationary during movement between the contracted and expanded states, but movable radially in relation to support members 26, 28, and 30 during movement between the contracted and expanded states. In the retracted/contracted state, the bends 18b, 20b, and 22b may be at or adjacent to the distal ends of the support members 26, 28, and 30. Distal ends of the first legs 18a, 20a, and 22a may be positioned within first tubes 26a, 28a, and 30a, respectively, and distal ends of the second legs 18c, 20c, and 22c may be positioned within the lumens of the second tubes 28b, 30b, and 26b, respectively. The longitudinal axes of the support members 26, 28, and 30 may be substantially parallel, and distal portions of each of the support members 26, 28, and 30 may be in contact with the other support members. Portions of the first legs 18a, 20a, and 22a and the second legs 18c, 20c, and 22c in the lumens of respective first or second tubes may be substantially parallel to one another. The support members 26, 28, and 30, and/or the outer sheath 12 may help to resist bowing of the movable members 18, 20, and 22 during movement of the device between the expanded and contracted states.

In the retracted/contracted state, the distal end of the coupler 46 may be spaced from the proximal ends of the support members 26, 28, and 30 by a distance 47. The distance 47 may be about 1 millimeter, although other distances may also be used. The proximal end of the coupler 46 may be spaced from the distal end of the sleeve 24 by a distance 49. The distance 49 may be about 16 millimeters, although other distances may also be used. In another example, distance 49 may be about 11 millimeters. Other distances 49 may position sleeve 24 in a more proximal position relative to a flexible ureteroscope channel where the ureteroscope scope does not deflect. This positioning may prevent binding of a rigid sleeve 24 within a curved portion of sheath 12. However, it is also contemplated that sleeve 24 may include one or more flexible materials. The distances 47 and 49 may vary based on the procedure being performed with the retrieval device 10.

Figure 2:
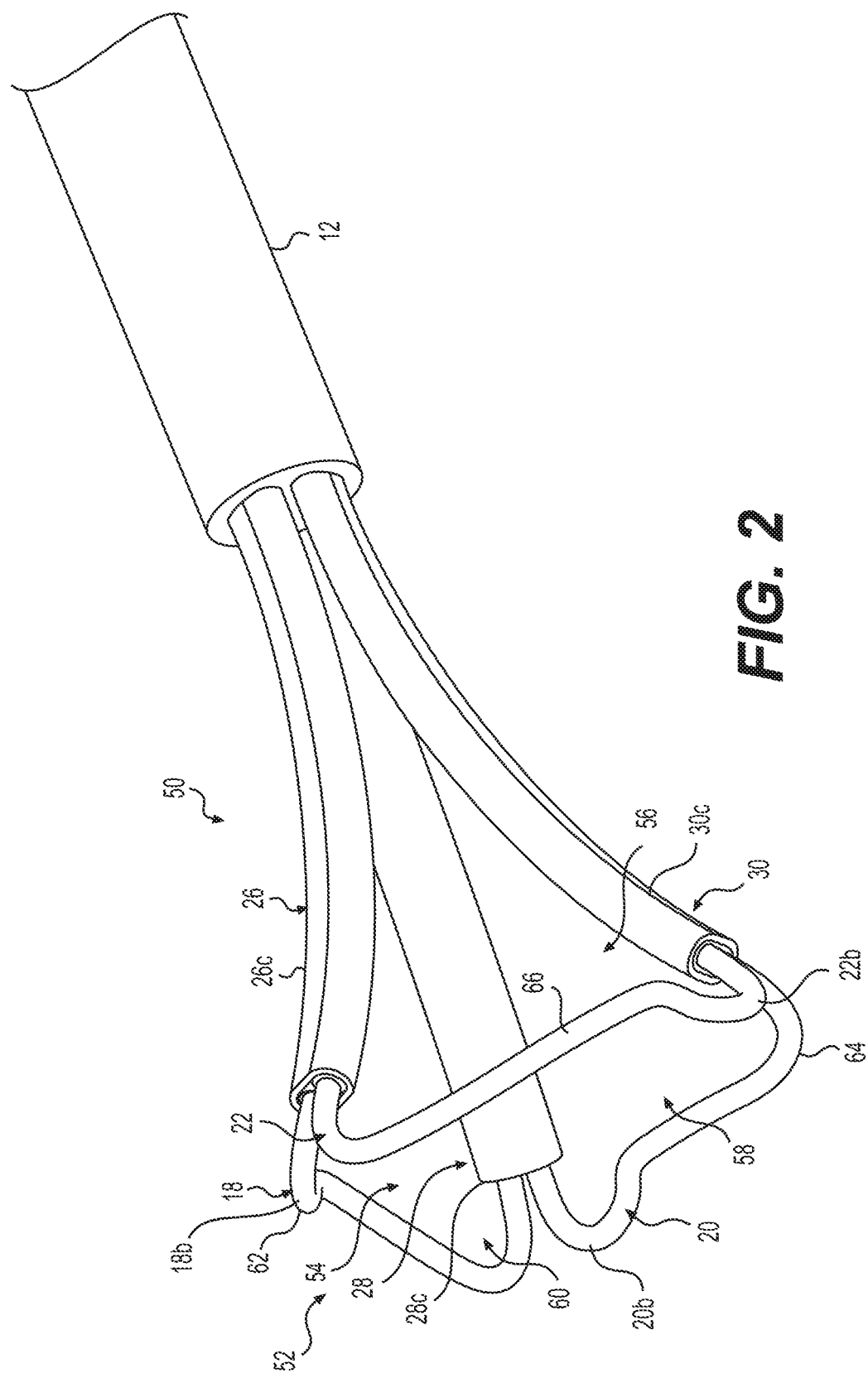
FIG. 2 is a perspective view of a distal end of the retrieval device of FIG.

In FIGS. 1 and 2, the retrieval device 10 is shown with the grasper portion 52 in an extended and expanded state. In the extended and expanded state, portions of the movable members 18, 20, and 22 may be exposed from the distal ends of the support members 26, 28, and 30 and the outer sheath 12. Once exposed, one or more of the movable members 18, 20, and 22 may move radially outwardly from the longitudinal axis of the outer sheath 12 due to a natural and/or applied radially outward biasing in one or more of the movable members 18, 20, and 22. Radially outward movement of one or more of the movable members 18, 20, and 22 may cause a corresponding radially outward movement of the support members 26, 28, and 30.

The exposed portions of the movable members 18, 20, and 22 may form bridges 62, 64, and 66 between the distal ends of the support members 26, 28, and 30. Each bridge may extend distally from the distal end of a given support member, and may be received in the distal end of an adjacent support member. The bridges 62, 64, and 66 may be formed by distal portions of the first legs 18a, 20a, and 22a, the bends 18b, 20b, and 22b, and distal portions of the second legs 18c, 20c and 22c.

Each bridge and its corresponding two support members may form a side loop of the grasper portion 52. Three side loops 54, 56, and 58 are shown in FIG. 2. The bridges 62, 64, and 66 may form a front loop 60 of the grasper portion 52 (a front loop 60 facing distally). Materials may enter the grasper portion 52 through one or more of the front loop 60 and the side loops 54, 56, and 58. By adding additional movable members and support members, additional side loops can be created.

Relative movement between drive member 16 and outer sheath 12 may cause grasper portion 52 to move to its extended and expanded state due to a natural and/or applied radially outward biasing in one or more of the movable members 18, 20, and 22. Extension and expansion of the grasper portion 52 may occur in phases. Starting from the retracted and contracted state shown in FIG. 3, a first phase of the extension and expansion of the grasper portion 52 may begin with movement of the drive member 16 distally relative to the outer sheath 12 and the support members 26, 28, and 30. The relative movement of the drive member 16 may cause the movable members 18, 20, and 22 and the coupler 46 to move distally relative to the outer sheath 12. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move distally relative to the outer sheath 12 and support members 26, 28, and 30 during the first phase. Proximal portions of the first legs 18a, 20a, and 22a may enter the lumens at the proximal end of first tubes 26a, 28a, and 30a, while proximal portions of second legs 18c, 20c, and 22c may enter the lumens at the proximal end of second tubes 28b, 30b, and 26b. Distal portions of the first legs 18a, 20a, and 22a, bends 18b, 20b, and 22b, and second legs 18c, 20c, and 22c may emerge from, or extend further out from, the distal ends of the support members 26, 28, and 30.

The coupler 46 forming the movable stop moves with the movable members 18, 20, and 22 relative to the outer sheath 12 and support members 26, 28, and 30. When the coupler 46 has traveled the distance 47 relative to the outer sheath 12 and support members 26, 28, and 30, further distal movement of the coupler 46 may be halted as the coupler 46 approaches the proximal ends of the support members 26, 28, and 30. This prevents the second legs 18c, 20c, and 22c from further entering the lumens of second tubes 28b, 30b, and 26b. At the end of the first phase of extension and expansion, the bends 18b, 20b, and 22b may each be spaced from distal ends of the support members 26, 28, and 30 by the distance 47 because the U-shaped bends 18b, 20b, and 22b are located a fixed distance from the coupler 46.

The presence of distance 47 between the support members 26, 28, and 30, and the coupler 46 facilitates the reciprocal movement of retrieval device 10 between the contracted and expanded states. That is, the presence of distance 47 reduces an initial amount of force required to move retrieval device 10 from the contracted state toward the expanded state. As described above, movable members 18, 20, and 22 may include a preset U-shape bend 18b, 20b, and 22b that serves to help clamp the distal end of the support members 26, 28, and 30 in the contracted state. By extending the movable members 18, 20, and 22 the distance 47, the clamping resistance of the U-shaped bends 18b, 20b, and 22b on the distal ends of the support members 26, 28, and 30 may be reduced. Moreover, movement of the movable members 18, 20, and 22 away from the distal end of the support members 26, 28, and 30 may provide a greater moment arm to overcome the bias of the U-shaped bends 18b, 20b, and 22b when moving the retrieval device 10 toward the expanded state.

The presence of distance 47 may also permit retrieval device 10 to form a first stage grasper by the portion of the movable members 18, 20, and 22 extending distally of the support members 26, 28, and 30. This first stage grasper can capture smaller fragments within only the portion of movable members 18, 20, and 22 extending distally from support members 26, 28, and 30 after movement of the distance 47. The distal ends of movable members 18, 20, and 22 may more securely capture smaller fragments than support members 26, 28, and 30 because they include a more distributed contact array or wire web than the support members 26, 28, and 30. It is noted that during the first phase movement of the movable members 18, 20, and 22, the support members extend generally parallel to one another. As understood, the word "generally" as used herein means mainly, and if more specificity is required, means a range of plus or minus eight percent of the relevant value.

A second phase of the extension and expansion of the grasper portion 52 may begin after distal movement of the coupler 46 has been halted. During the second phase, further distal movement of the drive member 16 relative to the outer sheath 12 and support members 26, 28, and 30 may drive distal movement of the first legs 18a, 20a, and 22a relative to the outer sheath 12 and support members 26, 28, and 30. During the second phase, the second legs 18c, 20c, and 22c may remain stationary relative to the support members 26, 28, and 30. The first legs 18a, 20a, and 22a may be increasingly exposed from the distal ends of the support members 26, 28, and 30, thereby increasing the lengths of the bridges 62, 64, and 66. Distal portions of the movable members 18, 20, and 22, and the support members 26, 28, and 30, may expand radially outwardly. The front loop 60 and the side loops 54, 56, and 58 may also expand in size.

Extension and expansion in the second phase may continue over the distance 49. Once the first legs 18a, 20a, and 22a have traveled the distance 49, distal movement of the drive member 16 may halt. Distal movement of the drive member 16 may be halted, for example, by a stop formed in the handle assembly shown in FIG. 1.

Moving the grasper portion 52 back to the retracted and contracted state may be accomplished by moving the drive member 16 proximally relative to the outer sheath 12 and support members 26, 28, and 30. Movement from the extended and expanded state to the retracted and contracted state may also occur in phases. A first phase of the retraction and contraction of the grasper portion 52 may begin with the drive member 16 moving proximally relative to the outer sheath 12. This may cause the first legs 18a, 20a, and 22a to move proximally relative to the outer sheath 12 and support members 26, 28, and 30. Distal portions of the first legs 18a, 20a, and 22a may enter the lumens at the distal ends of the first tubes 26a, 28a, and 30a. The second legs 18c, 20c, and 22c, and the coupler 46 may remain stationary relative to the support members 26, 28, and 30. The lengths of the bridges 62, 64, and 66 may decrease. The first legs 18a, 20a, and 22a, second legs 18c, 20c, and 22c, and support members 26, 28, and 30 may move radially inwardly. Thus, the front loop 60 and the side loops 54, 56, and 58 may decrease in size.

The first phase of the retraction and contraction of the grasper portion 52 may take place over the distance 49. Once the distance 49 has been covered, a second phase of the retraction and contraction may take place with continued movement of the drive member 16 proximally relative to the outer sheath 12 and the support members 26, 28, and 30. The continued movement may cause the movable members 18, 20, and 22 and the coupler 46 to move distally relative to the outer sheath 12 and support members 26, 28, and 30. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move proximally relative to the outer sheath 12 and support members 26, 28, and 30 during the second phase. Proximal portions of the first legs 18a, 20a, and 22a may exit the lumens at the proximal end of first tubes 26a, 28a, and 30a, while proximal portions of second legs 18c, 20c, and 22c may exit the at the proximal end of the second tubes 28b, 30b, and 26b. Distal portions of the first legs 18a, 20a, and 22a may enter into, or move further past the distal ends of first tubes 26a, 28a, and 30a, while the second legs 18c, 20c, and 22c may enter into, or move further past, the distal ends of the second tubes 28b, 30b, and 26b. The lengths of the bridges 62, 64, and 66 may decrease as the exposed lengths of the movable members 18, 20, and 22 decrease. As the bridges 62, 64, and 66 shrink, distal portions of the movable members 18, 20, and 22, and the support members 26, 28, and 30, may contract radially inwardly toward the longitudinal axis of the outer sheath 22. The front loop 60 and side loops 54, 56, and 58 may also shrink in size.

The coupler 46 may move with the movable members 18, 20, and 22 relative to the outer sheath 12 and support members 26, 28, and 30. When the coupler 46 has traveled the distance 47 relative to the outer sheath 12 and support members 26, 28, and 30, further proximal movement of the coupler 46 may be halted by operation of the handle assembly 90, such as a stop formed in the handle assembly 90 of FIG. 1. At the end of the second phase of retraction and contraction, the state shown in FIGS. 3-5 is attained. As noted above, in this contracted state, movable members 18, 20, and 22 may include preset U-shape bends 18b, 20b, and 22b located adjacent the distal ends of the support members 26, 28, and 30 that serve to help clamp the distal end of the support members 26, 28, and 30 in the contracted state.

Referring back to FIG. 1, the handle assembly 90 may be disposed at the proximal end 86 of the retrieval device 10. Handle assembly 90 may include an actuator 92 such as, e.g., a sliding mechanism, rotating mechanism, pushing mechanism, or the like. Actuator 92 may be coupled to outer sheath 12 and include internal stops for limiting movement of the outer sheath 12 relative to the movable members 18, 20, and 22. The drive member 16 may be fixed to a proximal end of the handle assembly 90. It is understood that the handle assembly may be formed in any conventional manner to control the movement of movable members 18, 20, and 22 relative to the outer sheath 12 and support members 26, 28, and 30 as described above. As noted above, handle assembly 90 may include one or more internal or external stops to limit movement of the movable members 18, 20, and 22.

Figure 6:
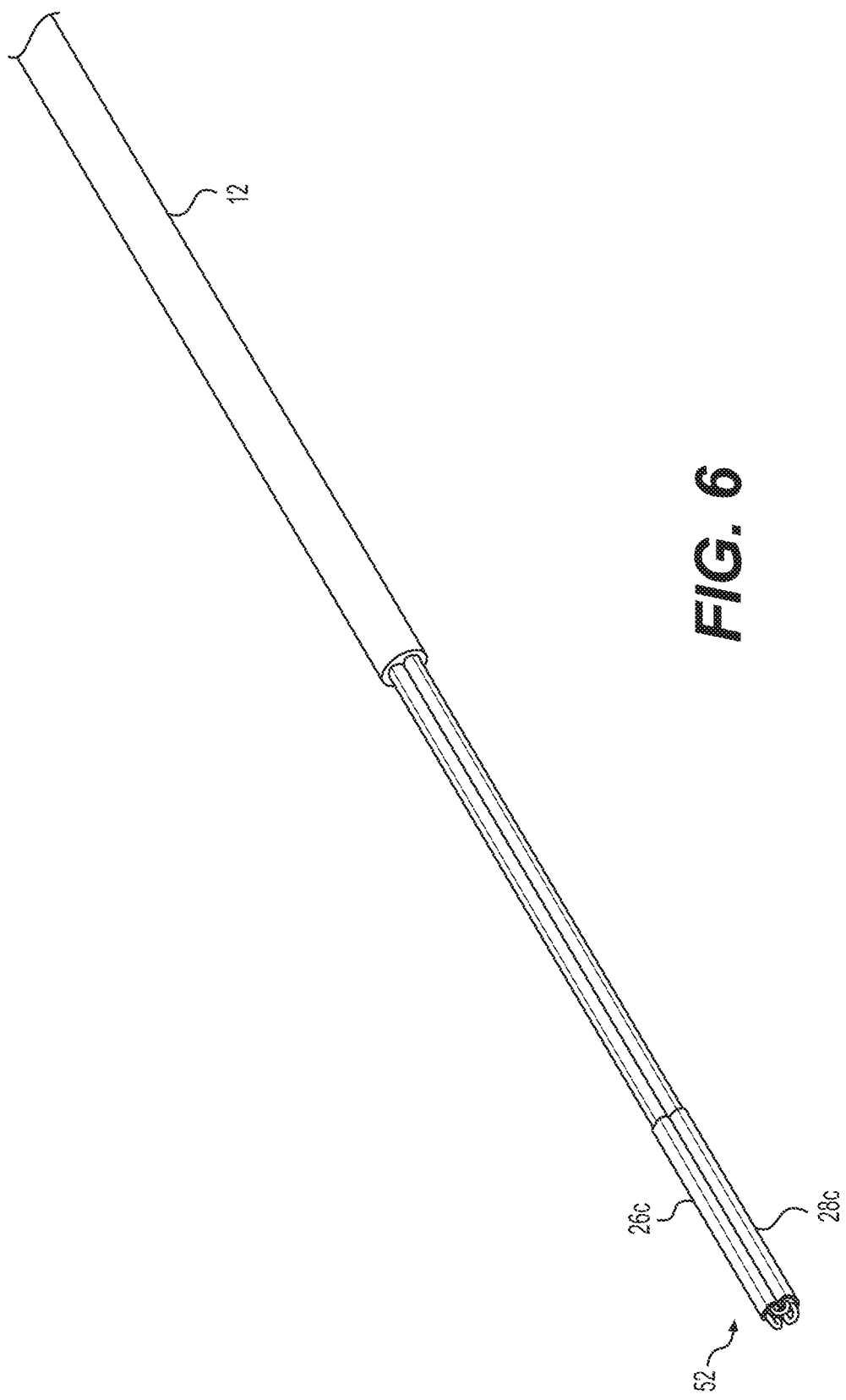
FIG. 6 is a perspective view of a distal end of a retrieval device, in accordance with another example of the present disclosure.
Figure 7:
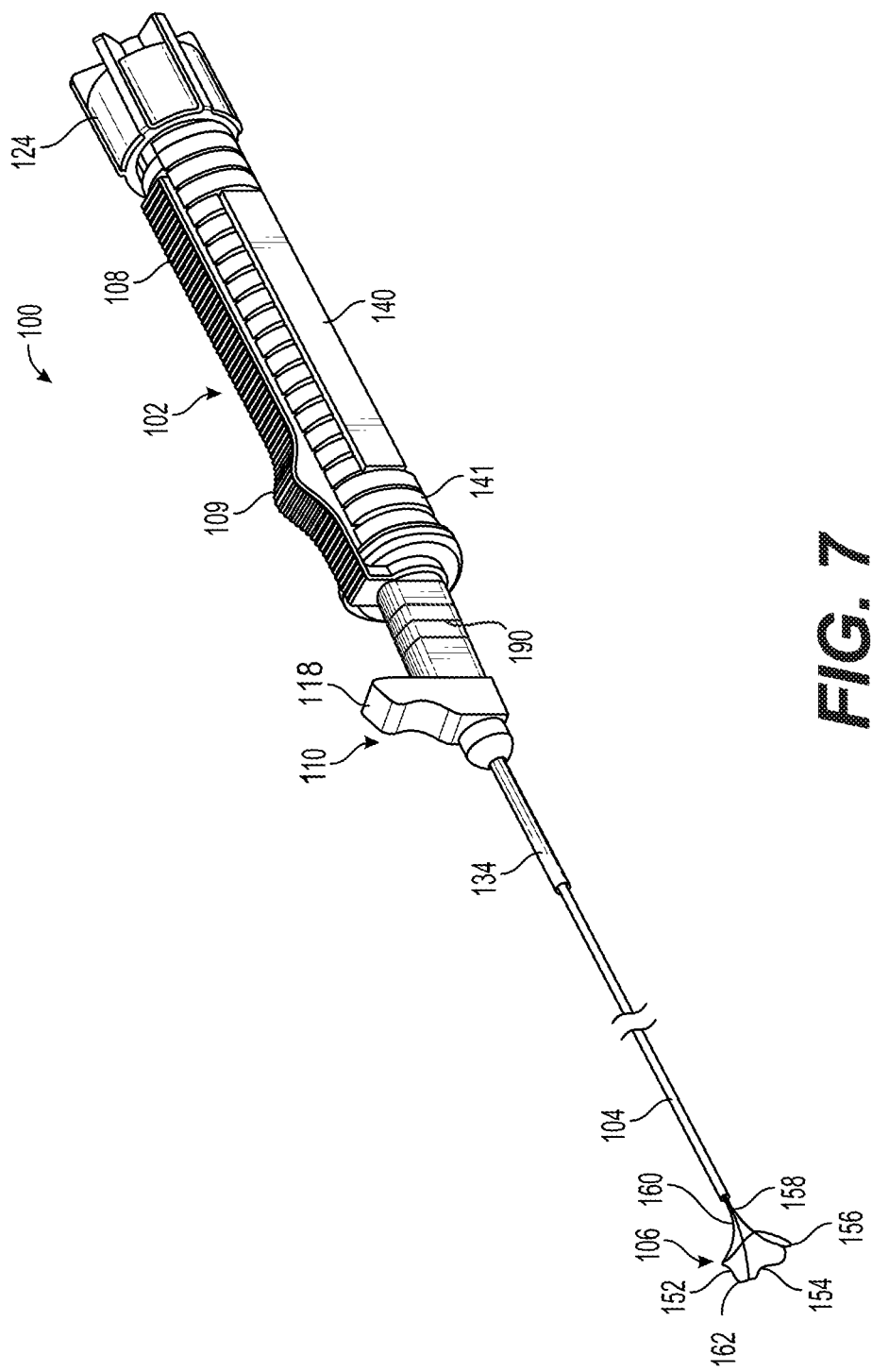
FIG. 7 is a perspective view of a retrieval device in an extended state, in accordance with another aspect of the present disclosure.

FIG. 6 depicts an alternative example of the grasper portion 52 in the retracted and collapsed configuration. The example of FIG. 6 may be substantially similar to the previous examples disclosed herein, except that the reinforcing members 26c, 28c, and 30c (not shown), may extend only along a portion of the exposed length of support members 26, 28, and 30. That is, reinforcing members 26c, 28c, and 30c, may be disposed only at a distalmost portion of support members 26, 28, and 30. Thus, at least a portion of the support members 26, 28, and 30 extending from sheath 12 may be exposed.

Figure 8:
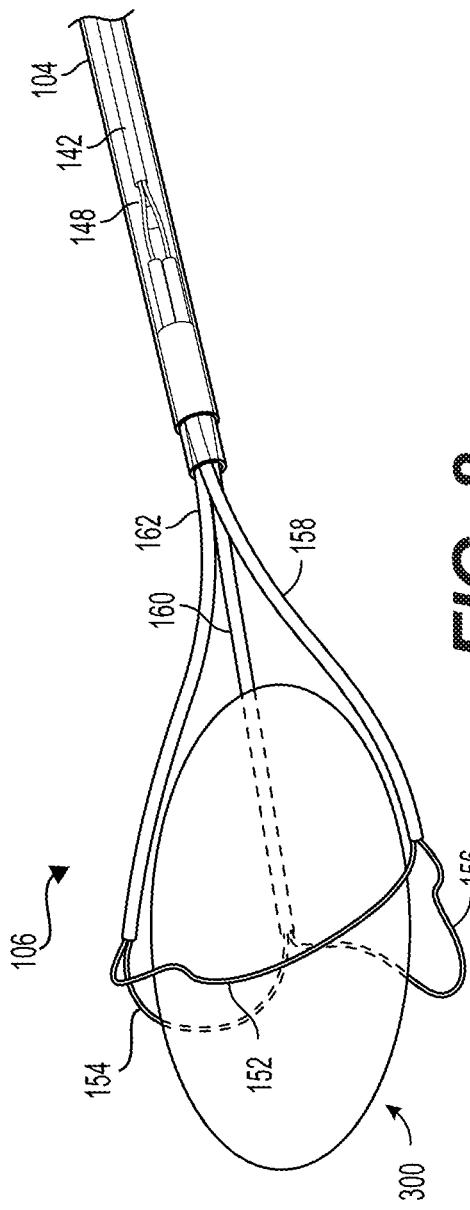
FIG. 8 is a perspective view of a distal end portion of the retrieval device of FIG. 7 in an extended state.
Figure 9:
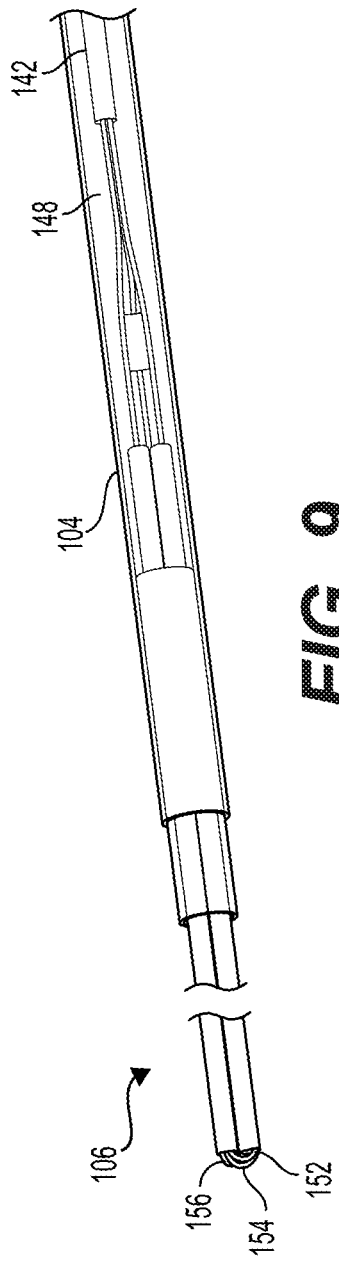
FIG. 9 is a perspective view of a distal end portion of the retrieval device of FIG. 7 in a retracted state.
Figure 10:
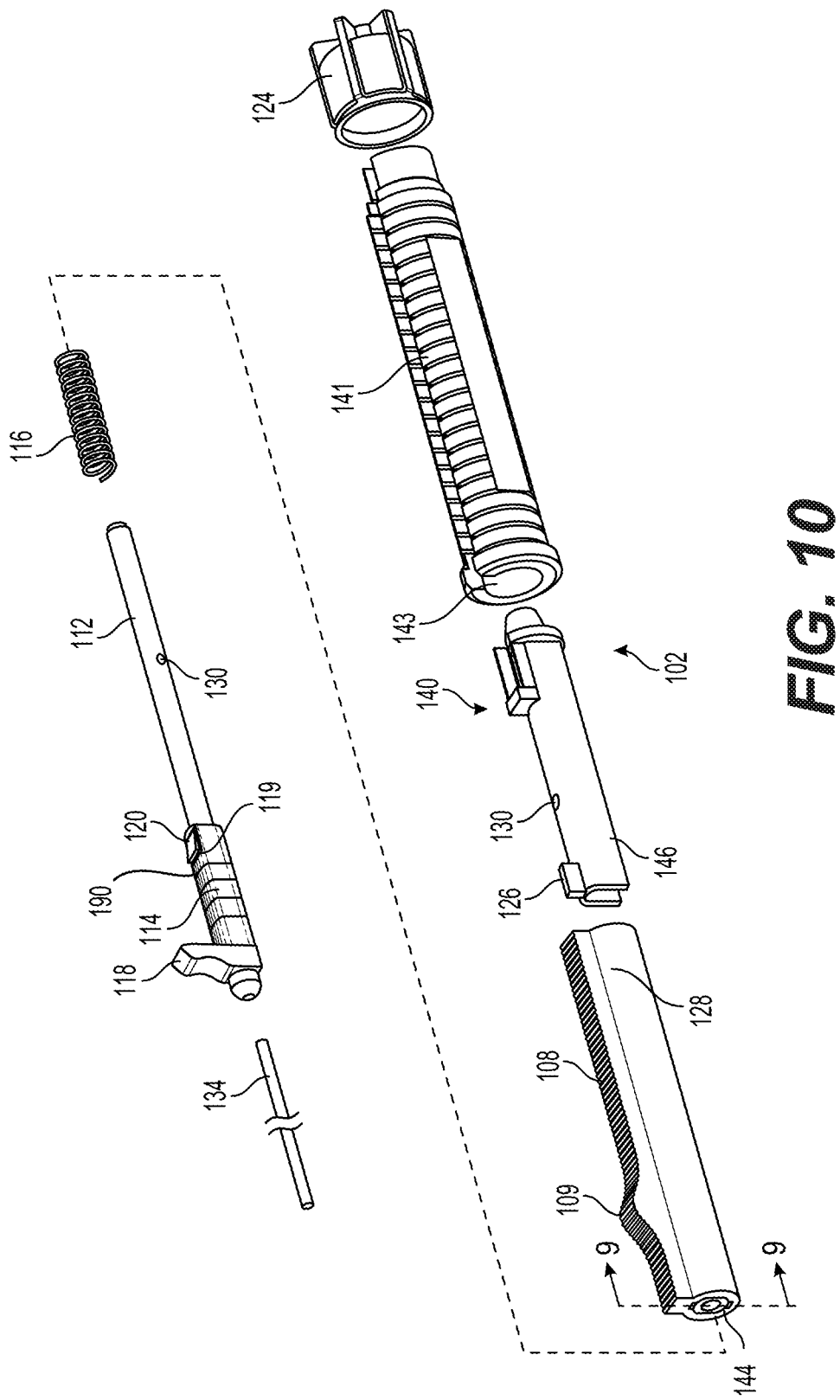
FIG. 10 is an exploded perspective view of portions of the retrieval device of FIG. 7.

FIGS. 7-16 show portions of a retrieval device 100 according to a first aspect of this disclosure. Retrieval device 100 may include a handle assembly 102 at the proximal end of the device 100, a sheath member 104, and an end effector 106 at the distal end of the device 100. The handle assembly 102 may include handle body 140 having handle cover 141, a first actuator or actuation member 108, and a second actuator 110. As shown in FIG. 10, second actuator 110 may take the form of a trigger assembly and may include various components, such as shaft 112, plunger 114, biasing member 116, and trigger 118. The second actuator 110 reciprocates within the first actuator 108. The first actuator 108 controls a maximum retracted state of the device 100 and the second actuator 110 controls a maximum extended state of the device 100.

Referring to FIGS. 7-10, the sheath member 104 of the device 100 may include a longitudinally-extending lumen. Sheath member 104 may be, for example, a hollow tube and may be manufactured using of any suitable material or combination of materials. Exemplary materials may include polymers or metals. Sheath member 104 may have any suitable features, for example, sheath member 104 may have varying flexibility, therapeutic coatings, visualization features (for direct visualization and/or viewing by an imaging device), surface features (e.g. protrusions, indentations, roughened portions), shape memory properties, etc. The sheath member 104 may have any suitable size and shape for insertion in the body. Portions of the sheath member 104 may be covered by various materials such as coatings and/or covers having various suitable properties. For example, a strain relief member 134 may be operatively coupled to the trigger assembly 110 and may extend at least partially over a proximal portion of sheath member 104. The strain relief member 134 may have any suitable size and shape for extending over sheath member 104 and decreasing distortion of sheath member 104 and may be manufactured using any suitable materials or combination of materials.

As shown in FIGS. 8-14, the retrieval device 100 may also include a shaft member 142, which may extend through a lumen 148 of the sheath member 104 and the handle assembly 102. The shaft member 142 may be elongated, and may include, for example, one or more wires, braids, shafts, etc. configured to transfer translational and/or rotational forces from its proximal end to its distal end. As will be explained in more detail below, the sheath member 104 may be movable relative to the shaft member 142 to close and open portions of the end effector 106.

Referring to FIGS. 7-10, the end effector 106 may have first, second, and third capture members 152, 154, and 156. While three capture members are shown, one or more additional capture members may also be included. It is also contemplated that fewer than three capture members may also be included. Each of capture members 152, 154, and 156 may be manufactured using any suitable material or combination of materials including, but not limited to, metals, polymers, or a combination of materials. For example, one or more of capture members 152, 154, and 156 may be formed with a shape memory material, such as Nitinol, and may be treated to possess an internal bias causing one or more of capture members 152, 154, and 156 to move radially outwardly away from the longitudinal axis of sheath member 104 in the absence of a constraining force.

Each of capture members 152, 154, and 156 may have any suitable cross-sectional shape, including cylindrical, elliptical, polygonal, and/or irregular. One or more of the capture members 152, 154, and 156 may include a portion flattened, machined, extruded, drawn, and/or etched into a different profile than a remaining portion. One or more of capture members 152, 154, and 156 may be slotted to allow deflection or directional bending. Exterior surfaces of the one or more of capture members 152, 154, and 156 may be roughened, notched, slotted, etched, sand-blasted, or otherwise modified to provide a better gripping surface.

Capture members 152, 154, and 156 may be operatively coupled to the shaft member 142. For example, proximal ends of capture members 152, 154, and 156 may be fixedly attached to a distal end of the shaft member 142 (now shown). The attachment may be provided by one or more of a splice joint, adhesives, melting, welding, crimping, joining using a heat shrinkable sleeve, and/or any other suitable attachment mechanism or process.

End effector 106 also may include first, second, and third support members 158, 160, and 162. Each of the support members 158, 160, and 162 may include a lumen (not shown) extending longitudinally therethrough. For example, support members 158, 160, and 162 may be a hollow tube. Support members 158, 160, and 162 may be disposed circumferentially about the longitudinal axis of the sheath member 104. Longitudinal axes of support members 158, 160, and 162 may be disposed at equal intervals circumferentially about the longitudinal axis of sheath member 104. Any other suitable number of support members and spacing configurations may alternatively be utilized.

Each support member 158, 160, and 162 may have any suitable cross-sectional shape, including cylindrical elliptical, polygonal, and/or irregular. One or more of support members 158, 160, and 162 may include a portion flattened, machined, extruded, drawn, and/or etched into a different profile than a remaining portion. Support members 158, 160, and 162 may be made of a flexible material, so that they may bend when being inserted into and through tortuous passages in a subject's anatomy. One or more of support members 158, 160, and 162 may be slotted to allow deflection or directional bending. Exterior surfaces of one or more of support members 158, 160, and 162 may be roughened, notched, slotted, etched, sand-blasted, or otherwise modified to provide a better gripping surface. Support members 158, 160, and 162 may be made of any suitable material, or combination of materials such as polymers (e.g. polyimide, or polyethylene terephthalate), and or metals (e.g. Nitinol), etc.

As shown in FIGS. 8 and 9, proximal portions of support members 158, 160, and 162 are received in a distal end of sheath member 104. For example, proximal portions of one or more of support members 158, 160, and 162 may be covered by a distal portion of sheath member 104, leaving a distal length exposed from the distal end of sheath member 104. Proximal portions of support members 158, 160, and 162 may be fixed relative to sheath member 104. For example, via a sleeve or heat-shrinkable sleeve and/or adhesive, such as an ultraviolet light curable adhesive or cyanoacrylate. The proximal ends of support members 158, 160, and 162 may be stationary relative to the distal end of sheath member 104, while allowing distal portions of the support members 158, 160, and 162 to move relative to the distal end of sheath member 104 and relative to one another between the exemplary portions shown in FIGS. 8 and 9.

Each support member 158, 160, and 162 may contact the other two support members. For example, each of the proximal portions of the support members 158, 160, and 162 may contact the proximal portions of the other two support members, such that support members 158, 160, and 162 may have a triangular arrangement around the longitudinal axis of sheath member 104. Longitudinal axes of support members 158, 160, and 162 may form vertices of a triangle, and portions of the longitudinal axes may be parallel. Distal portions of support members 158, 160, and 162 may be movable towards and away from the longitudinal axis of sheath member 104. The number of support members 158, 160, and 162 may be equal to the number of capture members 152, 154, and 156. It is contemplated that the number of support members and capture members may vary based on the type of procedure being performed.

Each of capture members 152, 154, and 156 may extend distally from shaft member 142, and may enter a lumen of one of support members 158, 160, and 162 at its proximal end. Each of capture members 152, 154, and 156 may extend distally through the lumen of the support member, and may exit the lumen at the distal end of one of support members 158, 160, and 162. Each of capture members 152, 154, and 156 may then transition into a bend and may enter a lumen through the distal end of another one of support members 158, 160, and 162. Each of capture members 152, 154, and 156 may then extend proximally through the lumen, and may exit the lumen at the proximal end of one of support members 158, 160, and 162. After exiting, each of capture members 152, 154, and 156 may be operatively coupled together in any fashion, such as by a clamp, adhesive, melting, welding, friction fit, heat-shrinking, and/or any other suitable form of attachment. The capture members 152, 154, 156 are secured to allow for longitudinal movement within all of the support members 158, 160, 162. For example, during initial opening of the end effector 106, the capture members 152, 154, 156 may all move an initial distance within the support members 158, 160, 162 to relieve opening forces of the device. The initial distance may be any suitable predetermined distance that may be controlled by the placement of a stop.

Portions of capture members 152, 154, and 156 extending distally from shaft member 142 may extend alongside surfaces of a spacer to space those portions of capture members 152, 154, and 156 apart from the longitudinal axis of sheath member 104, to help guide capture members 152, 154, and 156 into the lumens of support members 158, 160, and 162.

Capture members 152, 154, and 156, and support members 158, 160, and 162, form the end effector 106. End effector 106 may form a basket or grasper having front and side openings for capturing target objects 300 in an open or extended state as shown in FIG. 8. In FIG. 9, end effector 106 is shown in a retracted or closed state. End effector 106 may be moved into its retracted or closed state by moving first actuator 108 in a distal direction indicated by arrow "C" (shown in FIG. 11) to in turn move the sheath member 104 and associated support members 158, 160, and 162 distally relative to the capture members 152, 154, and 156 and shaft member 142. Moving the support members 158, 160, and 162 over the capture members serves to close the end effector 106.

In the retracted state, bends formed in the capture members 152, 154, and 156 may be at or adjacent to distal ends of support members 158, 160, and 162, as shown in FIG. 9. Longitudinal axes of support members 158, 160, and 162 may be substantially parallel in the retracted state, and both proximal and distal portions of each of support members 158, 160, and 162 may be in contact with the other support members. Portions of capture members 152, 154, and 156 in the lumens of support members 158, 160, and 162 may be substantially parallel. Support members 158, 160, and 162, and/or sheath member 104 may counteract the inherent bias in capture members 152, 154, and 156, keeping portions of capture members 152, 154, and 156 from bending radially outwardly from the longitudinal axis of sheath member 104 in the retracted state.

In FIG. 11, end effector 106 is shown in an extended state. In the extended state, portions of capture members 152, 154, and 156 may be exposed from the distal ends of the support members 158, 160, and 162 due to withdrawal of the sheath member 104 in a proximal direction indicated by the arrow "O". This may be accomplished by movement of the first actuator or actuation member 108 in a proximal direction indicated by arrow "O" which may in turn move trigger assembly 110 proximally to move or withdraw the sheath member 104 and connected support members 158, 160, and 162 in a proximal direction. Once exposed, capture members 152, 154, and 156 may move radially outwardly from the longitudinal axis of sheath member 104 due to inherent radially outward biasing in capture members 152, 154, and 156. Radially outward movement of capture members 152, 154, and 156 may cause a radially outward movement of support members 158, 160, and 162. Alternatively, support members 158, 160, and 162 may be biased radially outwardly, and capture members 152, 154, and 156 may urge support members 158, 160, and 162 into the retracted and contracted state. Sheath member 104 and support members 158, 160, and 162 may be moved proximally relative to capture members 152, 154, and 156 to extend end effector 106, allowing end effector 106 to move to its extended state.

As best shown in the exploded view in FIG. 10, the first actuator or actuation member 108 may have a protrusion 109 on its upper surface, on which the user may exert forces using his or her thumb to move the first actuator 108 proximally to transition the end effector 106 to a fully open or partially open state and distally to a fully retracted, partially retracted, or a further retracted state. The first actuator 108 may have a generally "U" shape having a lumen therethrough, and may be slidably disposed within the handle cover 141 having a slot 143 through which the actuation member protrusion 109 may extend. The first actuator or actuation member 108 also may include a stroke limiter 128 (FIG. 11). The stroke limiter 128 may be a separated component such as a tube or may be formed on the first actuator 108. The handle cover 141 may have various surface features to help the user hold the device 100.

Figure 15:
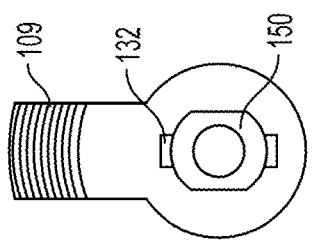
FIG. 15 is front view of a first actuator of the retrieval device along lines 15-15 of FIG. 10.

A locator body 146 may be disposed in a portion of the first actuator 108 lumen and may be operatively coupled to or formed within the handle body 140. The locator body 146 may have one or more protrusions or stops for controlling the longitudinal movement of the first actuator 108. For example, the locator body 146 may limit the sliding distance of the first actuator 108 by a distal stop 126 or proximal stop 147. The first actuator 108 may include a distal face 144 to operatively couple to portions of the trigger assembly 110. For example, FIG. 15 shows a front view of the first actuator 108 having a keyed front hole 150 to receive the trigger assembly 110.

The proximal end of the locator body 146 may include a vise 122 or any other suitable holding mechanism for holding shaft member 142. When vise 122 closes, shaft member 142 may be fixedly coupled. An end cap 124 may be placed onto the proximal end of the handle assembly 102 in any suitable manner (e.g. fasteners, adhesive, molding) to help close/clamp the vise around shaft member 142. For example, the handle assembly 102 may include an externally threaded portion (not shown), and end cap 124 may include complementary internal threading (not shown), so that end cap 124 may be screwed onto handle assembly 102.

The exterior surfaces of the locator body 146 may have any suitable size and shape and may correspond for disposal into lumen of the first actuator 108 having corresponding slots or grooves.

The trigger assembly 110 may be fixedly coupled to a proximal portion of the sheath member 104 in any suitable manner, such as fasteners, snap fasteners, insert molding, heat shrink, adhesive, weld, etc. For example, the plunger 114 may be insert molded on the sheath member 104. The trigger assembly 110 may be operatively coupled to the first actuator 108 in any suitable manner. For example, as shown in FIGS. 10 and 11-14, the trigger assembly 110 may include flexing tabs or flexing tabs 120, which may engage an interior surface of the first actuator 108. The flexing tabs 120 may be formed on the outer surface of the plunger 114 and may snap into corresponding slots. In other embodiments, the flexing tabs 120 may be replaced by keyed tabs, fasteners, screws, or any other suitable couplings that allow limited two-way movement of the plunger 114 relative to first actuator 108. The shaft member 142 may extend proximally through the sheath member 104 and a lumen of the trigger assembly 110, and the lumen 150 in the first actuator 108, and may be operatively coupled to the handle assembly 102 at vise 122.

In some embodiments, the trigger assembly 110 may be operatively coupled to the first actuator 108 by a set screw and slot coupling (not shown). In this embodiment, one or more screw holes may be formed in a distal portion of the first actuator 108, and a portion of the plunger 114 may include matching slots for each screw hole. Screws may be threaded into the screw holes to be aligned and extended into the slots in the plunger 114. The screw may limit the sliding distance of the plunger 114. The limit of longitudinal movement of the plunger 114 may be limited to the abutment of the screw to each end of the slot in the plunger 114.

The biasing member 116, such as a spring, may be disposed over a portion of the shaft 112 of the trigger assembly 110. The trigger 118 of the trigger assembly 110 may extend from the plunger 114. A user may exert forces on the trigger 118 of the trigger assembly 110 using his or her thumb or index finger. Any suitable materials or combination of materials having any suitable properties may be used to form the components of the handle assembly 102. For example, metals or polymers. The plunger 114 and shaft 112 may have any suitable size and shape. For example, the plunger 114 may have flat, planar exterior surfaces for keyed coupling with the first actuator 108, and the shaft 112 may have a round tubular shape over which biasing member 116, such as a spring, may be disposed.

FIG. 10 shows partially unassembled portions of device 100 in which cap 124 may be used to join the handle cover 141, the shaft member 142, and locator body 146 together. To assemble, the shaft member 142 may be placed and located between portions of the vise 122. The handle cover 141 may be slid over the internal parts (e.g. first actuator 108 and locator body 146) of the handle assembly 102. The cap 124 when tightened onto the handle cover and about the vise 122, may compress the vise 122, locking the shaft member 142, locator body 146, handle cover 141, and cap 124 together allowing the first actuator 108 to slide relative to the locator body 146.

As noted above, the internal components of the handle assembly 102 may be assembled by inserting the stroke limiter 128 of a particular length for a particular size end effector 106 in the first actuator 108. The stop 126 of the locator body 146 may be aligned with the first actuator 108 and the locator body 146 may be disposed into the first actuator 108. Prior to insertion into the handle body 140, the plunger 114 may be fixed to the sheath member 104 in any suitable manner, for example, insert molded, or glued. The biasing member 116 may be positioned on to the shaft 112 of the trigger assembly 110, and the trigger assembly may be inserted into the keyed front hole 150 of the first actuator 108. The keyed hole 150 may have any suitable shape and size that may limit rotational movement of the plunger 114 about the first actuator 108 and to allow torque transfer from the handle assembly 102 to the sheath member 104. The plunger 114 may have a shape that corresponds to the keyed front hole 150 of the first actuator 108. The shaft 112 may be inserted and aligned through the front keyed hole 150 and extended through a mid-hole 130 of the first actuator 108, as shown in FIG. 11. The shaft member 142 may be disposed in the vise 122. The flexing tabs 120 may be aligned to the keyed front hole 150 and may snap into place. The shaft member 142 may be trimmed to a suitable length so that the cap 124 can be assembled at final assembly of the device 100.

The plunger 114 may move a distance shown in FIG. 11 and FIG. 12. The user may use his or her thumb to move the plunger 114 in one direction via the trigger 118 and the biasing member 116 may return the plunger 114 back in the opposite direction. As the sheath member 104 is directly fixed to the plunger 114, changing the length of the plunger 114 relative to the first actuator 108 moves the length of the sheath member 104 relative to the first actuator 108, which in turn moves the end effector 106.

As described above, the device 100 may be used to retrieve a target object, such as organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. The device 100 may be used for single hand use while the other hand may be used to manipulate another portion of the device 100 or another device, such as an ureterscope. In this manner, using the trigger 118 and the first actuator 108, the user may manipulate and maneuver both the device 100 and any other device (e.g. a scope) without the aid of an assistant. The user may use the two actuators—the first actuator or actuation member 108 and the second actuator or trigger assembly 110 to manipulate the retraction and/or extension of the sheath member 104 relative to the capture members 152, 154, and 156 to open and close the end effector 106.

As shown in FIG. 8 the end effector 106 may be extended or opened to capture the target object 300. In order to accomplish this, the actuation member protrusion 109 may be gripped and the first actuator 108 may be moved proximally relative to the handle body 140 and the shaft member 142 along the locator body 146 and shaft 112. In an extended or open state as shown in FIG. 11, a proximal end of the first actuator 108 may abut with a proximal protrusion of the locator body 146. As first actuator 108 moves proximally, the sheath member 104 may withdraw proximally to expose the capture members 152, 154, and 156 allowing the end effector 106 to expand or open. This proximal movement is accomplished by the abutting connection of the proximal end of the plunger 114 to the first actuator 108 by flexing tabs 120, and the connection of the distal end of the plunger 114 to the sheath member 104.

As shown in FIG. 12, the trigger assembly 110 may be used to further extend or open the end effector 106. The trigger 118 may be actuated to move the trigger assembly 110 in the proximal direction. The trigger 118 may be operated with the index finger or the thumb to pull the trigger 118 proximally. Proximal movement of the trigger assembly 118 may compress the biasing member 116 and further withdraw the sheath member 104 proximally an additional distance to further extend or open the end effector 106 beyond its normal operating range (diameter) for the purposes of capturing a larger target through its front opening, releasing a stuck target object, or to enlarge the side opening of the end effector 106 to allow larger side opening target object capture. Upon release of the trigger 118, the biasing member 116 may return the plunger 114 back to its original stroke length (FIG. 11). The change in the length of the biasing member 116 may be equal to the movement of the sheath member 104 relative to the first actuator 108.

FIG. 13 shows the end effector 106 in a standard or fully closed or retracted state. The retracted state may be accomplished by moving the first actuator 108 distally a distance having a stroke length "S" starting at a position S1 (corresponding to a distal end of the stroke limiter 128) and moving to a position near stop 126. The actuation member protrusion 109 may be gripped and the first actuator 108 may be moved distally relative to the handle body 140 and the shaft member 142 along the locator body 146 and shaft 112. In a retracted state as shown in FIG. 13, the sheath member 104 may be urged over the capture members 152, 154, and 156 to retract the end effector 106.

FIG. 14 shows the end effector in a further retracted state in which the first actuator 108 may be further pushed in a distal direction an additional stroke length "A" for a total stroke length "T" from the fully retracted state shown in FIG. 13 at which the stroke limiter 128 travel from position S1 to a position abutting stop 126 to maintain retraction of the end effector 106. This state may be advantageous, for example, when the device 100 is traversing a tortuous path in the body, and the end effector 106 may require the assistance of the biasing member 116 to maintain the end effector 106 in a closed or retracted state. In this further retracted state, the standard stroke length "S" may be increased by an additional "A" closure length. The additional closure length "A" may assure sufficient sheath member 104 length to slide over the end effector 106 and may provide tactile confirmation that the end effector 106 is fully retracted. Any movement of 108 beyond the maximum distal movement of sheath member 104 (as defined by the capture members limiting movement of the support members distally), may result in displacement of the biasing member 116 to cause the biasing member 116 to compress. In turn, the compression of the biasing member 116 controls the stresses at the end effector 116 in the closed position, in that the spring force replaces the force applied to the first actuator or actuation member 108. As the first actuator 108 is released, the biasing member 116 may return the flexing tabs 120 back to the back side of the first actuator 108, and the sheath member 104 to an extended length as shown in FIG. 13. Thus, the biasing member 116 allows for a lost motion connection between the first actuator 108 and the second actuator 116. In addition, the first actuator 108 may transfer a force to the biasing member 116 when the first actuator 108 moves in the distal direction. The biasing member 116 is configured to reduce the force, and transfer the reduced force to the sheath member 104, when the force on the first actuator 108 exceeds a predetermined value. As the first actuator 108 moves distally relative to the handle body 104, the additional distance A beyond the first distance S, the biasing member 116 compresses as the first actuator 108 moves the additional distance A.

For example, as the sheath member 104 is restricted from moving in the distal direction by the bends of the movable member 152, 154, and 156 for closure, the continued movement of the first actuator 108 in the distal direction compresses the biasing member 116 a predetermined distance "x" against the plunger 114. The force that the compressed biasing member 116 exerts on the plunger 114 which, is connected directly to the sheath member 104 is in accordance with Hooke's law $F=Kx$ discussed above, where K is the spring constant and x is equal to the additional distance A shown in FIG. 13. Since the biasing member 116 is compressed initially during the assembly of the plunger 114 to the first actuator 108, $F=Kx$, where $x=A+x$, where x1=the free length of the biasing member 116—the initial compressed length of the biasing member 116. The force exerted by the biasing member 116 on the sheath member 104 and support tubes 158, 160, and 162 at the end of stroke distance A is greater than the stroke distance S, since the change of the length of the biasing member 116 is greater at the end of stroke A. At the end of stroke S, the biasing member 116 may be biasing the plunger 114 against the first actuator 108, thus and no spring force may be exerted to the sheath member 104. The closed or retracted state shown in FIG. 13 in which the first actuator 108 moves a stroke distance S to completely close the end effector 106 and further movement of the first actuator 108 the additional stroke distance A may provide an additional closure force.

The biasing member 116 may have any suitable properties according to Hooke's law. For example, the biasing member 116 may have any suitable spring constant K, such as between 0.700 lb./in and 0.900 lb./in. In some embodiments, the biasing member 116 may have a K value of about 0.872 lb./in. The biasing member 116 may have any suitable load height, for example, an initial load height of about 1.130" producing an initial spring force of about 0.104 lbf (0.047 kgf). The biasing member 116 may have any suitable expansion force such as no more than about 0.7 lbf (0.32 kgf) when the biasing member 116 is compressed about 18 mm to force the plunger 114 to extend distally and to return the length of the sheath member 104 to its initial length. A force of about 0.25 lbf (0.11 kgf) may be of sufficient force to advance the sheath member 104 over the shaft member 142 further compressing the biasing member 116 to advance the sheath member 104 to close the end effector 106 when the first actuator 108 is moved in the distal direction. In one embodiment, the size of the end effector 106 may be between 30 to about 70% larger in the release state shown in FIG. 12 than in the extended state shown in FIG. 11. For example, the maximum standard open size of the end effector 106 in the extended state (FIG. 11) may be about 8 mm in diameter and the trigger assembly 110 may further extend the open size to about 15 mm in the release state (FIG. 12). The biasing member 116 provides a neutral bias to the first actuator 108 when the end effector 106 is in the extended state shown in FIG. 11.

The device 100 also may provide stroke relief when the device is actuated. For example, distal movement of sheath member 104 coupled to the plunger 114 may be restricted when the device is in the closed or retracted position with the end effector 106 is empty, or when the end effector 106 is holding an object. Movement of the first actuator 108 in the distal direction when the sheath is retracted will compress the biasing member 116 a predetermined distance against the plunger 114. The force that the compressed biasing member 116 exerts on the plunger 114, which is fixed to the sheath member 104 is $F=Kx$ (Hooke's law), where K is the spring constant and x is equal to the change in the length of the biasing member 116 delta x, since the biasing member 116 may be initially compressed during assembly of the plunger 114 to the first actuator 108. Then $F=Kx$ where x equal delta x+x1 where x1=(free length of the biasing member 116)—(the initial compressed length of the biasing member 116).

The force exerted by the compressed biasing member 116 on the sheath member 104 and support tubes 158, 160, and 162 may be less than the force applied directly by the first actuator 108 if the biasing member 116 were not present, thus relieving or controlling the stroke force. The biasing member 116 may have any suitable K constant.

Referring to FIGS. 7 and 10-14, second actuator 110 may include one or more markers 190 that may provide a visual indication on handle assembly 102 that a stone or fragment is captured within end effector 106, and that may provide a visual indication of an estimate of the size of the captured stone or fragment. Markers 190 may be incorporated directly into a mold of second actuator 110, may be laser etched into second actuator 110, printed onto second actuator 110, or may be in any other suitable form. The markers 190 may be spaced at regular intervals from one another. For example, multiple markers 190 may be evenly spaced from one another. In other examples, the spacing between adjacent markers 190 may be irregular. Adjacent markers 190 may have different colors to indicate different sizes of objects disposed within end effector 106. In other examples, each marker 190 may be associated with a scaled number, e.g., 1 mm, 3 mm, or another suitable value, to indicate the size of a stone or fragment disposed within the end effector 106. Each marker 190 may be a line or other mark associated with a corresponding indicia, such as, e.g., 1 mm, 3 mm, or another suitable size to communicate the relative size of an object captured within the end effector 106.

When a stone is disposed within end effector 106 while end effector 106 is in the expanded configuration shown in FIG. 11, first actuator 108 may be slid distally to close the end effector 106. When the stone or object is disposed within the end effector 106, it may prevent the capture members 152, 154, and 156, from fully retracting into support members 158, 160, 162, even as first actuator 108 is pushed further distally. In these instances, further movement of the first actuator 108 distally will cause biasing member 116 to compress, and the first actuator 108 to advance over the proximal end of the second actuator 110. As first actuator 108 moves distally relative to second actuator 110, an operator may use markers 190 to approximate or otherwise determine the size of a stone or fragment captured within end effector 106.

The spacers 190, may be evenly spaced such that each marker represents 1 mm of diameter of the open end effector 106. As stones may range from 1 mm to 20 mm in size, a multi-line marker may indicate the progression of every 5 mm of space. For example, for the first 5 mm, a bold line may be marked, for the second 5 mm, a double bold line may be marked, and so forth enabling easy reading of total distance opened. The markings can also indicate if the stone will fit through the lumen of an access sheath. If the stone's perimeter is too large to fit through the sheath, the user may want to reposition the stone to a narrow orientation, or elect to fragment the stone to smaller pieces. A fully expanded basket also may be positioned next to a stone to allow the user to visually gauge the stone size.

Larger stones or fragments captured by end effector 106 may cause biasing member 116 to compress more than smaller stones or fragments, and, therefore, may cause more relative movement between the second actuator 110 and first actuator 108. The operator may compare the position of markers 190 on second actuator 110 to a reference location on first actuator 108, such as, e.g., a distal end 192 (shown only in FIG. 11) of first actuator 108 to determine the approximate size of a stone or object captured within end effector 106. As discussed above, the positions of the various markers 190 may correlate to the compression of biasing member 116, and thus may correlate to the size of the stone or fragment captured within end effector 106. The length of biasing member compression can be approximated by a perimeter of the captured stone divided by the number of capture members (e.g., divided by three when there are three capture members). In some examples, the perimeter may be the length that is being ligated by the capture members. This may correlate to the perimeter of the stone at the positions where the, e.g., three, capture members are ligating the stone. If the stone burden is somewhat circular in cross section at the point of ligation, then the approximation may be close. Using the circumference equation $C=2\pi r$, the approximated diameter of the stone can be calculated. The spring also may limit the hand force that can be applied to the sheath and support members during capturing of a stone burden. The restoring force limitation of the spring may prevent over-stressing or deformation of the component such as, e.g., capture member stretching, or compression of the sheath to obtain a consistent measurement.

A spring selection with an appropriate spring rate K may help control or limit the magnitude of the restoring force. Using hook's law F equals Kx, the restoring force F can be determined where K is the spring constant and x equals (free length minus initial load height) plus (perimeter of the stone divided by the number of capture members). The restoring force that is applied by the spring to the sheath and support member may be the force that is applied to the spring by the user's hand via the first actuator 108. The magnitude of the spring length compression may be dependent upon the perimeter size of the stone burden being ligated by the capture members. The measurement of the stone burden may be measured at a full closed stroke of the first actuator 108. Even through the full length of the stroke may not needed, the full stroke length may ensure that the spring is subjected to a more than sufficient length of first actuator travel. If insufficient travel (e.g., shorter than the perimeter divided by the number of capture members) is reached, the spring may compress less than needed, leading to an incorrect measurement. The markers may be evenly spaced if a spring is used. The spacing between the markers may be calculated by the equation $\pi*d/3$, or 1.047 mm per 1 mm change in diameter of a circular perimeter, for example.

The markers 190 may allow operators to quickly, accurately, and easily estimate the size of a stone or stone fragment captured within end effector 106. Markers 190 may also serve as a visual indicator that a stone or fragment has been captured at all. That is, in some procedures, operators may attempt to capture a stone without visualization, e.g., in a calyx where the ureteroscope may be unable to deflect enough to provide direct visualization. In these examples, it may be difficult for a urologist to determine whether a stone or fragment has been captured. Markers 190 may provide a visual indication that a stone or fragment was indeed captured.

In one embodiment, a target object may be captured by opening the end effector 106 to its open diameter in the extended state (FIG. 11) and advancing the front opening of the end effector 106 towards the target object, capturing the object, moving the target object to a desired location. Actuating trigger assembly 110 may be moved proximally to further open the end effector 106 to the further extended or release state (FIG. 12), to grab or capture larger target objects. The trigger assembly 110 also may be advantageously used to open the end effector 106 during release of the object so that the end effector 106 may open to a larger size than the end effector 106 during capture of the target object. Thus, the trigger assembly 110 may be activated when the release state is needed or when a target object is stuck in the effector 106.

Figure 16:
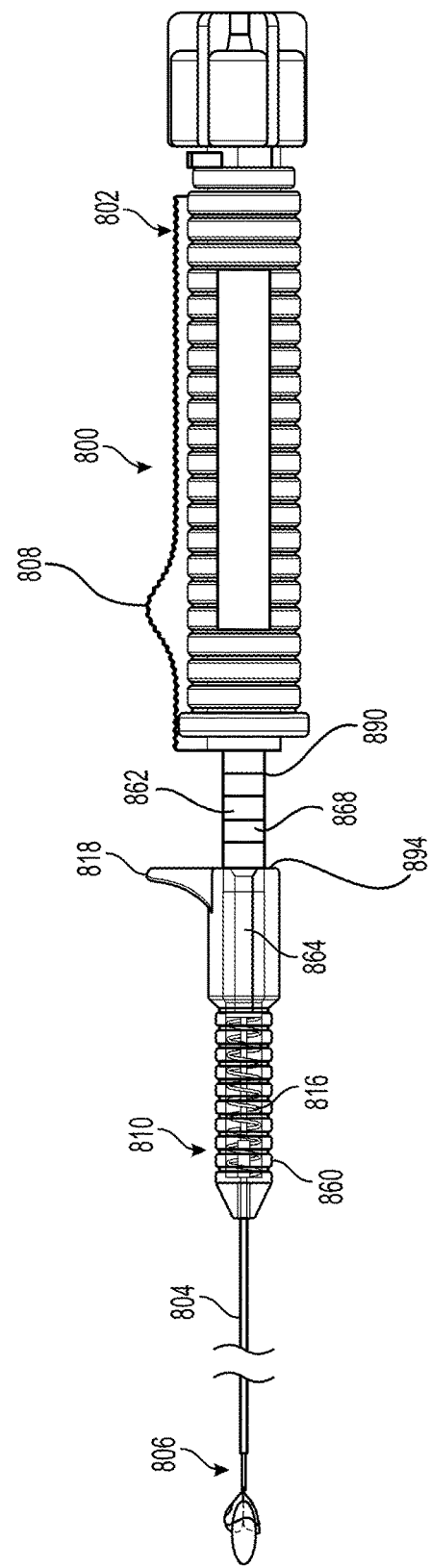
FIG. 16 is a partial cross-sectional side view of a portion of a retrieval device in an extended state.
Figure 17:
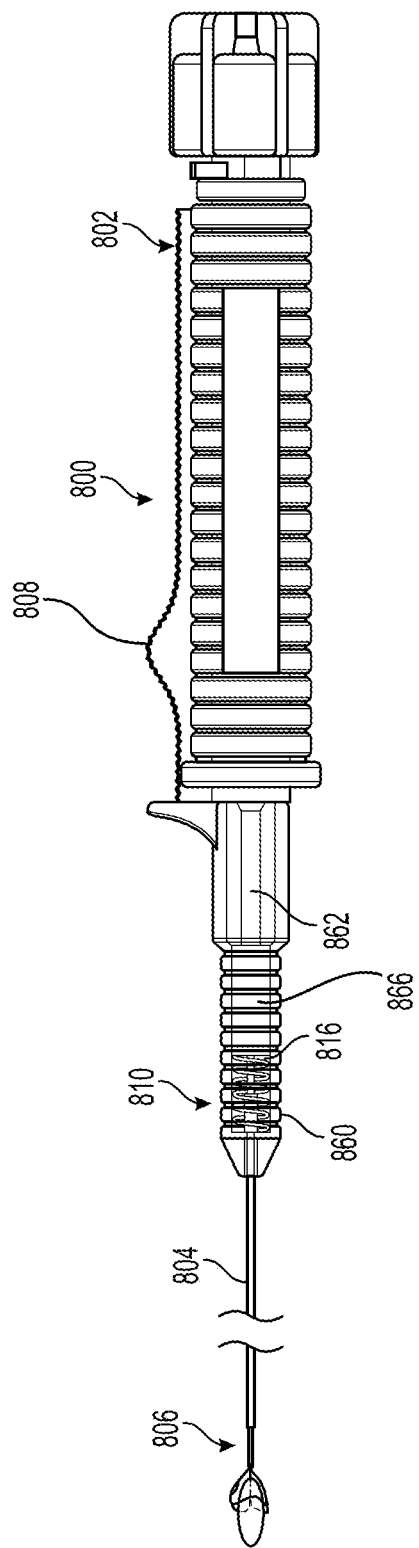
FIG. 17 is a partial cross-sectional side view of a portion of the retrieval device of FIG. 16 in a further extended state.

FIGS. 16 and 17 show another embodiment of a medical retrieval device 800 similar to medical retrieval device 100 in which second actuator in the form of a trigger assembly 810 is external from handle assembly 802. Trigger assembly 810 may include a biasing member 816, a biasing member housing 860 for housing the biasing member 816 in the form of a spring, a piston body 862, and a trigger 818 extending from the biasing member housing 860. The distal end of the biasing member housing 860 may be fixed to the outer surface of the sheath 804 in any suitable manner, such as by glue, heat shrink, etc. In one aspect, the piston body 862 may include a snap trigger members that are recessed in opposing internal slots 864 in the biasing member housing 860. The proximal end of the biasing member housing 860 may be coupled to a portion of the piston body 862 in any suitable manner, such as via latches, fasteners, etc. The proximal end of the piston body 862 may be attached to the distal end of the actuation member 808 of the handle assembly 802 in any suitable manner, such as by threads, interference fit, glue etc. Alternatively, the actuation member 808 and the piston body 862 may be formed as a single part.

The piston body 862 may include a distal portion 866 of a first width or diameter and a proximal portion 868 of a second width or diameter. The distal portion 866 slides within a distal reduced opening in the biasing member housing 860 and the proximal portion 868 of the piston body 860 is received in a larger opening of the biasing member housing 860. The distal portion 866 of the piston body 862 includes an end face that abuts a proximal end of biasing member 816.

The trigger assembly 810 may be actuated to transition the device from the extended state shown in FIG. 16 to the further extended state shown in FIG. 17 by moving the trigger 818 in a proximal direction along piston body 862 towards the actuation member 808 to compress the biasing member 816, in turn withdraw the sheath 804, and support members. Actuation of the trigger assembly 810 moves the sheath 804 an additional distance to further extend or open the end effector 806 beyond its normal operating range (diameter) for the purposes of capturing a larger target objects through its front opening, releasing a stuck target object, or to enlarge the side opening of the end effector 806 to allow larger side opening target object capture. Upon release of the trigger 818, the biasing member 816 may return the biasing member housing 860 back to its original stroke length shown in FIG. 16. The change in the length of the biasing member 816 may be equal to the change in the length of the sheath member 804 relative to the actuation member 808. In some embodiments, the biasing member housing 860 may include relief slots extending therethrough, which may allow portions of the biasing member housing 860 to expand in various directions. For example, two relief slots may extend along a top portion and two relief slots may extend along a bottom portion of the biasing member housing 860. The biasing member housing 860 also may include a flexing tab or ramp portion at a proximal end for engaging a corresponding slot or opening on the piston body 862 and/or a slot for engaging a ramp.

As shown in FIG. 16, piston body 862 may include one or more markers 890 that may be substantially similar to markers 190 described above with reference to FIGS. 7 and 10-14. In this example, distal markers 890 may be covered by trigger assembly 818 when a stone is captured within the end effector 806. Thus, an operator may compare the position of a reference location on trigger assembly 810 (e.g., a proximal end 894 of trigger assembly 818) to the markers 890 to visually determine whether a stone or fragment has been captured, and to estimate the size of the captured stone or fragment.

Any features described herein with respect to a certain example may be used with any other example. For instance, the handle assembly 102 described with reference to FIGS. 7-15, or the trigger assembly 810 described with reference to FIGS. 16 and 17 may be utilized with the retrieval device 10 described with reference to FIGS. 1-6.

The disclosed retrieval devices may be utilized in any suitable application requiring the capture and removal of materials from the body. Any aspect set forth in any example may be used with any other example set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

The disclosed devices may be configured to capture fragments having dimensions of about 3 French or smaller. In some examples, the disclosed medical devices may be able to capture and release smaller stones having diameters from 1 millimeter to 12 millimeters. In some examples, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and the retrieval device may be removed from the human body. In some examples, a guide sheath for a ureteroscope may be used to guide the ureteroscope and retrieval device back to a previous position or to a new position to capture additional stones, and protect a ureter wall during stone removal. While moving from the extended and expanded state to the retracted and contracted state, retrieval devices of the present disclosure may ligate larger stones and capture smaller stones within the grasper portion 52.

It will be apparent to those skilled in the art that various modifications and variations can be made in the disclosed systems and processes without departing from the scope of the disclosure. For example, the retrieval device disclosed could include more than three support members, such as four or five support members, and an equal number or less movable members. Other examples of the disclosure will be apparent to those skilled in the art from consideration of the specification and practice of the features disclosed herein. It is intended that the specification and examples be considered as exemplary only.

We claim:

1. A retrieval device having a contracted state and an expanded state, comprising:
   a sheath;
   at least three support members each having at least two lumens, a proximal end fixed to the sheath, and a distal end movable relative to the sheath; and
   at least three movable members movable relative to the support members, each movable member extending through a lumen of one support member of the at least three support members and through a lumen of a different support member of the at least three support members, wherein:

each of the at least three movable members is configured to slide distally within more than one of the at least three support members during transition of the retrieval device from the contracted state to the expanded state; and portions of the at least three support members and portions of the at least three movable members move radially outward relative to a central longitudinal axis of the retrieval device only after:

entireties of the at least three movable members move distally by a distance, while entireties of the at least three support members remain fixed in place, and after the entireties of the at least three movable members have moved the distance distally, first ends of the movable members are moved further distally.

2. The retrieval device of claim 1, wherein each support member includes a first tube defining one lumen of the at least two lumens, and a second tube defining another lumen of the at least two lumens.

3. The retrieval device of claim 2, wherein the first and second tubes of a given support member are fixed relative to one another.

4. The retrieval device of claim 2, wherein the first and second tubes of a given support member are substantially parallel to one another.

5. The retrieval device of claim 2, wherein each support member further includes a reinforcing member disposed around the first and second tubes, the reinforcing member is disposed at a distal end of the first and second tubes, and each support member includes a portion extending distally from the sheath that remains uncovered by the reinforcing member.

6. The retrieval device of claim 1, wherein each support member is parallel to a longitudinal axis of the sheath while the retrieval device is in the contracted state.

7. The retrieval device of claim 1, wherein the sheath encompasses at least a portion of the movable members and at least a portion of the support members.

8. The retrieval device of claim 1, further including a stop located at a second end of at least one movable member of the at least three movable members to restrict movement of the second end after moving the distance distally, wherein the stop includes a coupling securing second ends of the at least three movable members together.

9. The retrieval device of claim 1, wherein each of the at least three movable members includes a U-shaped bend located distally of the distal ends of the at least three support members, and the U-shaped bend is preformed and urges the support members toward the contracted state.

10. The retrieval device of claim 1, further including a handle assembly having a handle body, a reference location, and an actuator movable relative to the handle body, the actuator having a plurality of markers spaced apart from one another, wherein the at least three movable members are configured to capture objects, and the capture of objects of different sizes causes the plurality of markers to move to different positions relative to the reference location to allow a user of the retrieval device to visually estimate a size of a captured object.

11. The retrieval device of claim 1, wherein entireties of each of the at least three movable members are movable distally and proximally relative to each of the at least three support members.

12. The retrieval device of claim 1, wherein after the entireties of the at least three movable members are moved distally by the distance, second ends of the at least three movable members are prevented from moving further distally.

13. A retrieval device, comprising:

a sheath;

at least three pairs of tubes disposed at a distal end of the sheath, wherein each of the pairs of tubes are movable between a contracted configuration and an expanded configuration, and each of the pairs of tubes are parallel to a longitudinal axis of the sheath in the contracted configuration, and are configured to bow radially outward from the longitudinal axis of the sheath in the expanded configuration; and at least three movable members, each movable member forming a bridge between two different pairs of tubes of the at least three pairs of tubes, wherein portions of the at least three pairs of tubes and portions of the at least three movable members move radially outward relative to a central longitudinal axis of the retrieval device only after entireties of the at least three movable members move distally while entireties of the at least three pairs of tubes remain fixed in place.

14. The retrieval device of claim 13, wherein the tubes of a given pair of tubes of the at least three pairs of tubes are fixed relative to one another.

15. The retrieval device of claim 13, wherein the retrieval device includes three bridges formed by the at least three movable members, wherein the three bridges form a distally-facing loop when the at least three pairs of tubes are in the expanded configuration.

16. The retrieval device of claim 13, wherein each bridge forms a side loop with the two different pairs of tubes that the bridge is between.

\* \* \* \* \*